(12) United States Patent
Melcher et al.

(10) Patent No.: US 9,576,312 B2
(45) Date of Patent: *Feb. 21, 2017

(54) DATA MESH-BASED WEARABLE DEVICE ANCILLARY ACTIVITY

(71) Applicant: eBay Inc., San Jose, CA (US)

(72) Inventors: Ryan Melcher, Ben Lomond, CA (US); John Tapley, San Jose, CA (US); Robert Lee, Burlingame, CA (US)

(73) Assignee: eBay Inc., San Jose, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 14/498,326

(22) Filed: Sep. 26, 2014

(65) Prior Publication Data

US 2015/0281009 A1    Oct. 1, 2015

Related U.S. Application Data

(60) Provisional application No. 61/970,263, filed on Mar. 25, 2014.

(51) Int. Cl.
*H04L 29/06* (2006.01)
*G06Q 30/06* (2012.01)
(Continued)

(52) U.S. Cl.
CPC ...... *G06Q 30/0631* (2013.01); *G06Q 30/0633* (2013.01); *G06T 11/206* (2013.01);
(Continued)

(58) Field of Classification Search
CPC ...... G06T 11/206; H04L 43/04; H04L 61/609; H04L 63/08; H04L 63/107; H04L 67/10; G06Q 30/0633; G06Q 30/0631
(Continued)

(56) References Cited

U.S. PATENT DOCUMENTS 5,794,178 A    8/1998  Caid et al.
6,014,661 A    1/2000  Ahlberg et al.
(Continued)

FOREIGN PATENT DOCUMENTS

WO    WO-2015148559 A1    10/2015

OTHER PUBLICATIONS

U.S. Appl. No. 14/449,126, filed Jul. 31, 2014, Data Mesh Based Environmental Augmentation.
(Continued)

*Primary Examiner* — Harunur Rashid
(74) *Attorney, Agent, or Firm* — Schwegman Lundberg & Woessner, P.A.

(57) ABSTRACT

In various example embodiments, a system and method for data mesh-based wearable device ancillary activity are presented. A device activity being performed in real-time by a user device of a user is detected. Attribute data associated with a plurality of attribute sources is accessed. A user preference indicating a preference for performing on a secondary user device a complementary activity corresponding to the device activity is inferred. Based on the inferred user preference, the secondary user device is identified according to a device status of the secondary user device, the device status indicating a device capability to perform the complementary activity in real-time. The complementary activity to be performed in real-time on the secondary user device is generated by analyzing at least one of the device activity, a device functionality of the secondary user device, and the user preference. Instructions to perform the complementary activity in real-time are transmitted to the secondary user device.

14 Claims, 17 Drawing Sheets

(51) Int. Cl.
 *G06T 11/20* (2006.01)
 *H04L 12/26* (2006.01)
 *H04L 29/12* (2006.01)
 *H04L 29/08* (2006.01)

(52) U.S. Cl.
 CPC ............ *H04L 43/04* (2013.01); *H04L 61/609* (2013.01); *H04L 63/08* (2013.01); *H04L 63/107* (2013.01); *H04L 67/10* (2013.01)

(58) Field of Classification Search
 USPC ........................................................ 709/224
 See application file for complete search history.

(56) References Cited

U.S. PATENT DOCUMENTS

| | | | |
|---|---|---|---|
| 6,097,386 | A | 8/2000 | Bardon et al. |
| 6,137,499 | A | 10/2000 | Tesler |
| 6,301,579 | B1 | 10/2001 | Becker |
| 7,483,964 | B1* | 1/2009 | Jackson .............. H04L 12/2809 455/41.1 |
| 8,095,432 | B1 | 1/2012 | Berman et al. |
| 8,463,939 | B1 | 6/2013 | Galvin |
| 8,686,924 | B2 | 4/2014 | Braun et al. |
| 8,908,926 | B2 | 12/2014 | Henderson et al. |
| 2002/0149614 | A1 | 10/2002 | Biebesheimer et al. |
| 2002/0161664 | A1 | 10/2002 | Shaya et al. |
| 2003/0073412 | A1 | 4/2003 | Meade, II |
| 2003/0229895 | A1 | 12/2003 | Jasinschi et al. |
| 2007/0143250 | A1 | 6/2007 | Zigon |
| 2007/0174331 | A1 | 7/2007 | Wolf |
| 2007/0244844 | A1 | 10/2007 | Brinson et al. |
| 2007/0299796 | A1* | 12/2007 | Macbeth ................ G06Q 10/10 706/16 |
| 2008/0015953 | A1 | 1/2008 | Harper et al. |
| 2008/0092245 | A1 | 4/2008 | Alward et al. |
| 2008/0207220 | A1 | 8/2008 | Aaron |
| 2008/0222706 | A1 | 9/2008 | Renaud et al. |
| 2009/0309891 | A1 | 12/2009 | Karkanias et al. |
| 2010/0128988 | A1 | 5/2010 | Kincaid |
| 2010/0153868 | A1 | 6/2010 | Allen et al. |
| 2010/0231418 | A1 | 9/2010 | Whitlow et al. |
| 2011/0046805 | A1 | 2/2011 | Bedros et al. |
| 2011/0093780 | A1 | 4/2011 | Dunn |
| 2011/0148916 | A1 | 6/2011 | Blattner |
| 2011/0153663 | A1 | 6/2011 | Koren et al. |
| 2012/0059787 | A1 | 3/2012 | Brown et al. |
| 2012/0096076 | A1* | 4/2012 | Chan .................... G06F 9/4856 709/203 |
| 2013/0006899 | A1 | 1/2013 | Cook |
| 2013/0119255 | A1 | 5/2013 | Dickinson et al. |
| 2013/0238538 | A1 | 9/2013 | Cook et al. |
| 2013/0258118 | A1 | 10/2013 | Felt |
| 2013/0262588 | A1 | 10/2013 | Barak et al. |
| 2013/0275994 | A1* | 10/2013 | Uola ....................... G06F 9/542 718/106 |
| 2013/0297688 | A1 | 11/2013 | Zheng |
| 2013/0305185 | A1 | 11/2013 | Nicol, II et al. |
| 2013/0321446 | A1 | 12/2013 | Cutcher-gershenfeld et al. |
| 2014/0135644 | A1 | 5/2014 | Kim |
| 2014/0136365 | A1 | 5/2014 | Nista et al. |
| 2014/0173078 | A1 | 6/2014 | Mccord et al. |
| 2014/0176335 | A1 | 6/2014 | Brumback et al. |
| 2014/0189829 | A1 | 7/2014 | Mclachlan et al. |
| 2014/0279294 | A1 | 9/2014 | Field-darragh et al. |
| 2015/0127565 | A1 | 5/2015 | Chevalier et al. |
| 2015/0253445 | A1 | 9/2015 | Luo et al. |
| 2015/0262282 | A1 | 9/2015 | Walti et al. |
| 2015/0269151 | A1 | 9/2015 | Wallace |
| 2015/0278912 | A1 | 10/2015 | Melcher et al. |
| 2015/0279069 | A1 | 10/2015 | Melcher et al. |
| 2015/0281252 | A1 | 10/2015 | Melcher et al. |
| 2016/0012129 | A1 | 1/2016 | Rampson et al. |
| 2016/0048595 | A1 | 2/2016 | Vanblon et al. |
| 2016/0048993 | A1 | 2/2016 | Shimomura et al. |
| 2016/0049008 | A1 | 2/2016 | Haddick et al. |

OTHER PUBLICATIONS

U.S. Appl. No. 14/449,113, filed Jul. 31, 2014, Data Mesh Visualization.
U.S. Appl. No. 14/459,115, filed Aug. 13, 2014, Data Mesh Based Zero Effort Shopping.
"U.S. Appl. No. 14/449,113, Non Final Office Action mailed Feb. 26, 2016", 15 pgs.
"U.S. Appl. No. 14/449,126, Response filed Mar. 23, 2016 to Non Final Office Action mailed Oct. 23, 2015", 14 pgs.
"U.S. Appl. No. 14/459,115, Non Final Office Action mailed Feb. 26, 2016", 19 pgs.
Chen, et al., "Real-time smartphone sensing and recommendations towards context-awareness shopping", Springer-Verlag Berlin Heidelberg 2013, (Dec. 6, 2013), 61-72.
Yeh, et al., "Intelligent service-integrated platform based on the RFID technology and software agent system", journal homepage: www.elsevier.com/locate/eswa, Elsevier L TO, vol. 38, Issue 4, (Apr. 2011), 3058-3068.
"U.S. Appl. No. 14/449,126, Non Final Office Action mailed Oct. 23, 2015", 20 pgs.
Yu, et al., "Application mobility in pervasive computing: A survey", Pervasive and Mobile Computing, 1-17.
"U.S. Appl. No. 14/449,113, Final Office Action mailed Aug. 4, 2016", 21 pgs.
"U.S. Appl. No. 14/449,113, Response filed May 26, 2016 to Non Final Office Action mailed Feb. 26, 2016", 12 pgs.
"U.S. Appl. No. 14/449,126, Examiner Interview Summary mailed Sep. 22, 2016", 5 pgs.
"U.S. Appl. No. 14/449,126, Final Office Action mailed Jun. 17, 2016", 20 pgs.
"U.S. Appl. No. 14/449,112, Response filed Dec. 5, 2016 to Final Office Action mailed Aug. 4, 2016", 15 pgs.
"U.S. Appl. No. 14/449,112, Non Final Office Action mailed Nov. 21, 2016", 20 pgs.
"U.S. Appl. No. 14/449,126, Response filed Oct. 17, 2016 to Final Office Action mailed Jun. 17, 2016", 14 pgs.
Park, et al., "Design patterns for context-aware services", Springer Science+Business Media New York 2014, Multimed Tools Appl (2015) 74:2337-2358 DOI 10.1007/s11042-014-2001-7, (Apr. 23, 2014), 22 pgs.

* cited by examiner

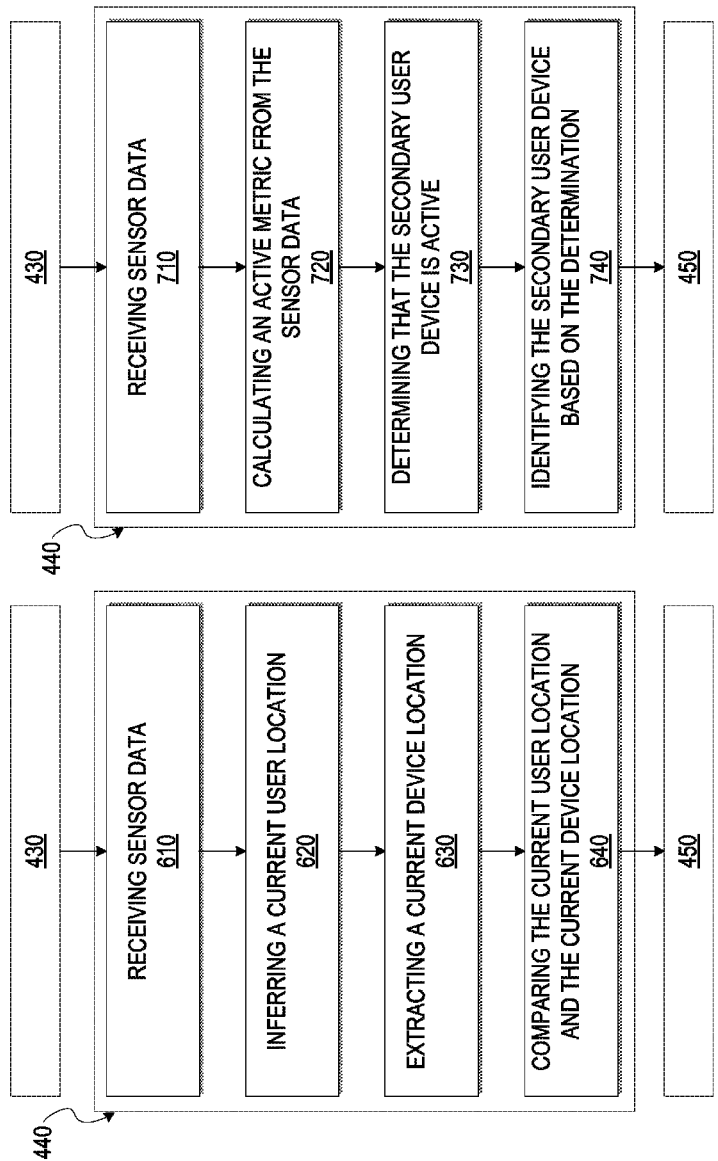

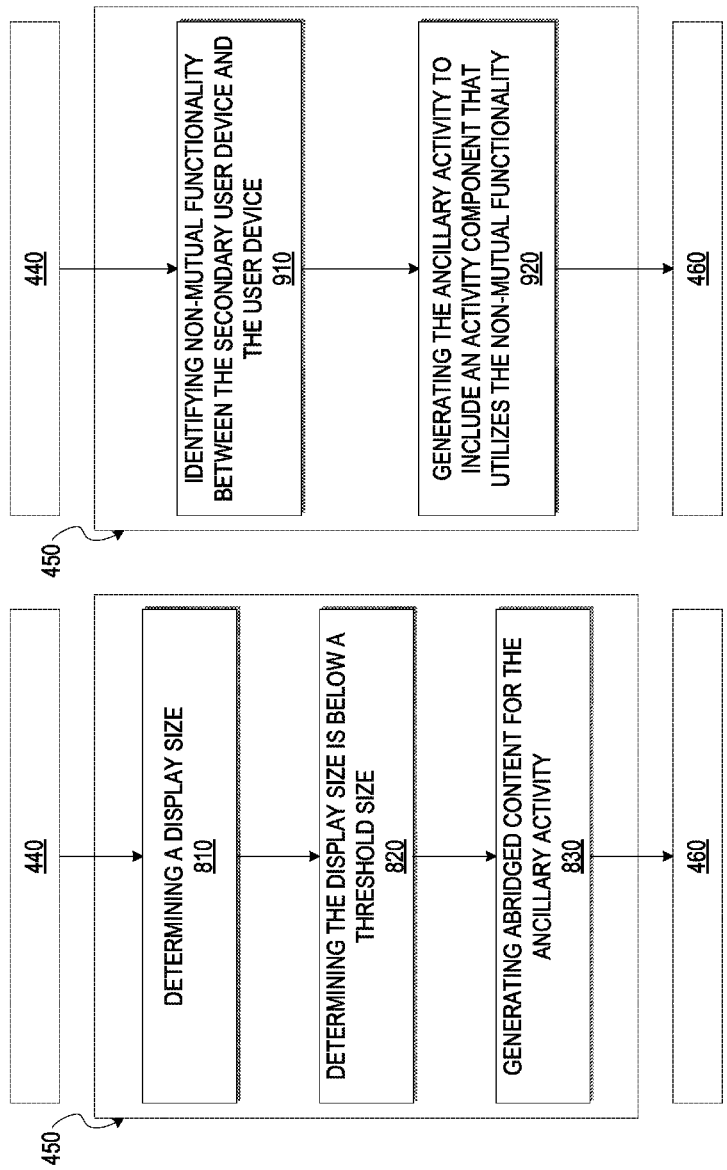

DATA MESH-BASED WEARABLE DEVICE ANCILLARY ACTIVITY

RELATED APPLICATIONS

This application claims the priority benefit of U.S. Provisional Application No. 61/970,263, entitled "PORTABLE PROFILE PLATFORM," filed Mar. 25, 2014, which is hereby incorporated by reference in its entirety.

TECHNICAL FIELD

Embodiments of the present disclosure relate to data mesh-based wearable device ancillary activity.

BACKGROUND

In recent years, mobile devices, wearable devices, smart devices, and the like have pervaded nearly every aspect of modern life. Such devices are increasingly incorporating sensors to monitor everything from the moisture level of houseplants to a dribbling of a basketball. Network-connected devices like these are capable of providing a near real-time and constant data feed. These trends have provided a vast amount of rich, constantly updated data.

BRIEF DESCRIPTION OF THE DRAWINGS

Various ones of the appended drawings merely illustrate example embodiments of the present disclosure and should not be considered as limiting its scope.

FIGS. 6 and 7 are flow diagrams illustrating further operations for facilitating identifying a secondary user device, according to some example embodiments.

FIGS. 8 and 9 are flow diagrams illustrating further operations for generating an ancillary activity for a secondary user device, according to some example embodiments.

Figure 1:
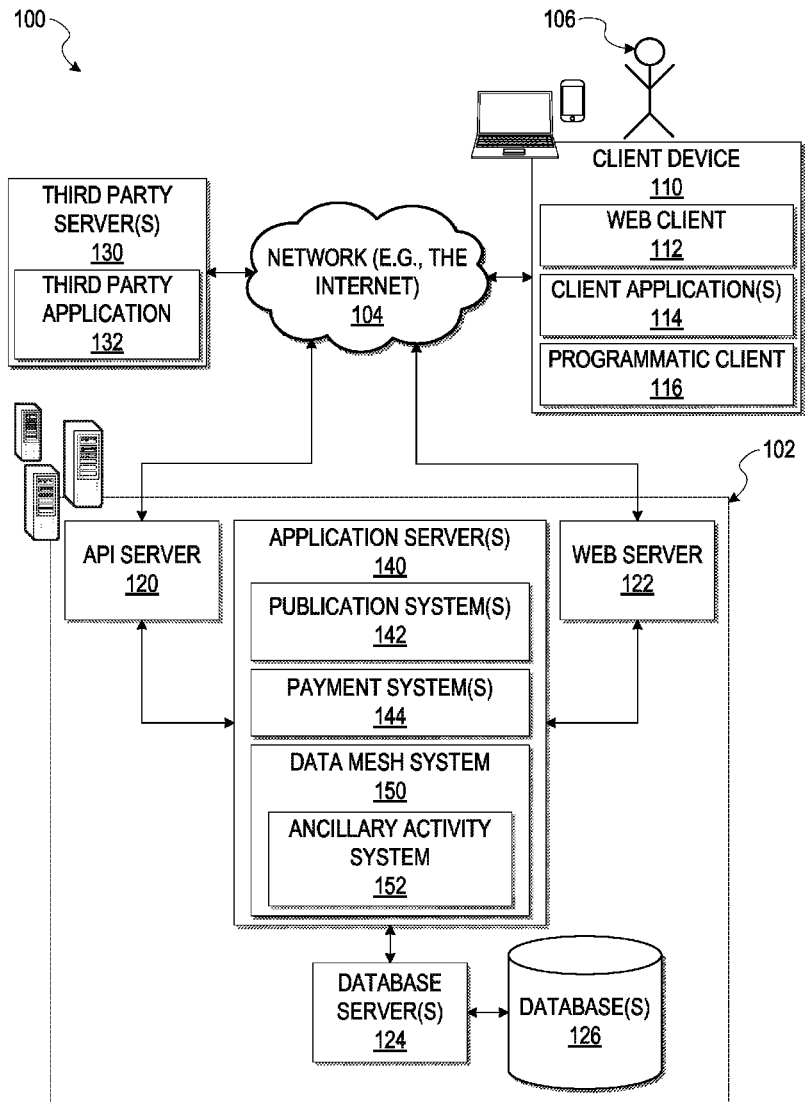
FIG. 1 is a block, diagram illustrating a networked system, according to some example embodiments.

The headings provided herein are merely for convenience and do not necessarily affect the scope or meaning of the terms used.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

Modern users of technology typically have a variety of devices to perform various tasks such as laptop computers, smart televisions, smart phones, wearable devices. Traditionally, a user of such devices operates a single device to perform a task at one time. The discussion below describes systems and methods that, in some embodiments, utilize multiple devices to perform, in real-time, an ancillary, complementary, or supplemental activity associated with a particular activity or task. In some embodiments, the systems and methods distribute a portion a particular activity or task across multiple devices. The ancillary or supplemental activity associated with a particular device activity may be determined based on a variety of factors including an inferred user preference, device functionality, and the device activity. Thus, the ancillary activity is dynamically determined and performed for the user in real-time to assist the user with the device activity.

In various example embodiments, a device activity being performed in real-time by a user device of a user is detected. For example, the user may be browsing a website on a mobile device or a laptop computer. Once the device activity is detected, attribute data associated with the user from a plurality of attribute sources is accessed. In various example embodiments, the attribute data is received or accessed from a broad range of attribute sources such as, for example, from mobile devices, smart devices, smart homes, social network services, user profiles, browsing histories, purchase histories, and so forth.

A user preference indicating a preference or desire of the user for performing on a secondary user device an ancillary, supplemental, complementary, or companion activity corresponding to the device activity. For example, an analysis of the attribute data can indicate the user would like to view supplemental content corresponding to the device activity.

In this example, the ancillary activity comprises presenting the supplemental content to the user on the secondary user device.

Based on the inferred user preference, the secondary user device can be identified according to a device status of the secondary user device, according to some example embodiments. In various implementations, the device status indicates a device capability to perform the ancillary activity in real-time. For example, if the ancillary activity comprises presenting content to the user, the secondary user device may be incapable of performing such a task if the secondary user device is not within a vicinity of the user (e.g., within a presentation distance of the user).

Once the secondary user device is identified, the ancillary activity, to be performed in real-time on the secondary user device, is generated by analyzing the device activity, a device functionality of the secondary user device, and the user preference. For example, if the device activity comprises providing directions to the user, the ancillary activity may comprise providing content associated with providing directions such as a current heading or distance to destination readout. In various implementations, the ancillary activity is caused to be performed on the secondary user device or transmitted to the secondary user device with instruction to perform in real-time the ancillary activity.

With reference to FIG. 1, an example embodiment of a high-level client-server-based network architecture 100 is shown. A networked system 102 provides server-side functionality via a network 104 (e.g., the Internet or wide area network (WAN)) to a client device 110. A user (e.g., user 106) may interact with the networked system 102 using the client device 110. FIG. 1 illustrates, for example, a web client 112 (e.g., a browser, such as the Internet Explorer® browser developed by Microsoft® Corporation of Redmond, Wash.), client application(s) 114, and a programmatic client 116 executing on the client device 110. The client device 110 can include the web client 112, the client application(s) 114, and the programmatic client 116 alone, together, or in any suitable combination. Although FIG. 1 shows one client device 110, multiple client devices can be included in the network architecture 100.

The client device 110 can comprise a computing device that includes at least a display and communication capabilities that provide access to the networked system 102 via the network 104. The client device 110 comprises, but is not limited to, a remote device, work station, computer, general purpose computer, Internet appliance, hand-held device, wireless device, portable device, wearable computer, cellular or mobile phone, personal digital assistant (PDA), smart phone, tablet, ultrabook, netbook, laptop, desktop, multi-processor system, microprocessor-based or programmable consumer electronic, game consoles, set-top box, network PC, mini-computer, and the like. In further example embodiments, the client device 110 comprises one or more of a touch screen, accelerometer, gyroscope, biometric sensor, camera, microphone, global positioning system (GPS) device, and the like.

The client device 110 can communicate with the network 104 via a wired or wireless connection. For example, one or more portions of the network 104 can be an ad hoc network, an intranet, an extranet, a Virtual Private Network (VPN), a Local Area Network (LAN), a wireless LAN (WLAN), a Wide Area Network (WAN), a wireless WAN (WWAN), a Metropolitan Area Network (MAN), a portion of the Internet, a portion of the Public Switched Telephone Network (PSTN), a cellular telephone network, a wireless network, a Wireless Fidelity (Wi-Fi®) network, a Worldwide Interoperability for Microwave Access (WiMax) network, another type of network, or a combination of two or more such networks.

The client device 110 can include one or more of the applications (also referred to as "apps") such as, but not limited to, web browsers, book reader apps (operable to read e-books), media apps (operable to present various media forms including audio and video), fitness apps, biometric monitoring apps, messaging apps, electronic mail (email) apps, e-commerce site apps (also referred to as "marketplace apps"), and so on. The client application(s) 114 can include various components operable to present information to the user and communicate with networked system 102. In some embodiments, if the e-commerce site application is included in the client device 110, then this application can be configured to locally provide the user interface and at least some of the functionalities with the application configured to communicate with the networked system 102, on an as needed basis, for data or processing capabilities not locally available (e.g., access to a database of items available for sale, to authenticate a user, to verify a method of payment). Conversely, if the e-commerce site application is not included in the client device 110, the client device 110 can use its web browser to access the e-commerce site (or a variant thereof) hosted on the networked system 102.

In various example embodiments, the users (e.g., the user 106) can be a person, a machine, or other means of interacting with the client device 110. In some example embodiments, the users may not be part of the network architecture 100, but may interact with the network architecture 100 via the client device 110 or another means. For instance, the users can interact with client device 110 operable to receive input information from (e.g., using touch screen input or alphanumeric input) and present information to (e.g., using graphical presentation on a device display) the users. In this instance, the users may, for example, provide input information to the client device 110 to be communicated to the networked system 102 via the network 104. The networked system 102, in response to the received input information, communicates information to the client device 110 via the network 104 to be presented to the users. In this way, the user may interact with the networked system 102 using the client device 110.

An Application Program Interface (API) server 120 and a web server 122 may be coupled to, and provide programmatic and web interfaces respectively to, one or more application server(s) 140. In various implementations, the application server(s) 140 hosts one or more publication system(s) 142, payment system(s) 144, and a data mesh system 150, each of which comprises one or more modules or applications and each of which are embodied as hardware, software, firmware, or any combination thereof. The application server(s) 140 are, in turn, shown to be coupled to one or more database server(s) 124 that facilitate access to one or more information storage repositories or database(s) 126. In an example embodiment, the database(s) 126 are storage devices that store information to be posted (e.g., publications or listings) to the publication system(s) 142. The database(s) 126 stores digital goods information in accordance with some example embodiments.

Additionally, a third party application 132, executing on third party server(s) 130, is shown as having programmatic access to the networked system 102 via the programmatic interface provided by the API server 120. For example, the third party application 132, utilizing information retrieved from the networked system 102, supports one or more features or functions on a website hosted by the third party.

The third party website, for example, provides one or more promotional, marketplace, or payment functions that are supported by the relevant applications of the networked system 102.

The publication system(s) 142 provides a number of publication functions and services to the users that access the networked system 102. The payment system(s) 144 likewise provide a number of functions to perform or facilitate payments and transactions. While the publication system(s) 142 and payment system(s) 144 are shown in FIG. 1 to both form part of the networked system 102, it will be appreciated that, in alternative embodiments, each system 142 and 144 may form part of a payment service that is separate and distinct from the networked system 102. In some example embodiments, the payment system(s) 144 may form part of the publication system(s) 142.

The data mesh system 150 provides functionality to receive, retrieve, or store a broad spectrum of data associated with the users, according to various embodiments. It will be noted that the collective, aggregated attribute data is sometimes referred to as a "data mesh." The data mesh system 150 stores, for example, received data in storage devices such as the database(s) 126. In an example embodiment, the data mesh system 150 includes an ancillary activity system 152 that generates ancillary activities based on various triggers and information. In some example embodiments, the data mesh system 150 communicates with the client device 110, the third party server(s) 130, the publication system(s) 142 (e.g., retrieving listings), and the payment system(s) 144 (e.g., purchasing a listing). In an alternative example embodiment, the data mesh system 150 can be a part of the publication system(s) 142.

Further, while the client-server-based network architecture 100 shown in FIG. 1 employs a client-server architecture, the present inventive subject matter is, of course, not limited to such an architecture, and can equally well find application in a distributed, or peer-to-peer, architecture system, for example. The various systems of the applications server(s) 140 (e.g., the publication system(s) 142 and the payment system(s) 144) can also be implemented as stand-alone software programs, which do not necessarily have networking capabilities.

The web client 112 can access the various systems of the networked system 102 (e.g., the publication system(s) 142) via the web interface supported by the web server 122. Similarly, the programmatic client 116 and client application (s)) 114 can access the various services and functions provided by the networked system 102 via the programmatic interface provided by the API server 120. The programmatic client 116 can, for example, be a seller application (e.g., the Turbo Lister application developed by eBay® Inc., of San Jose, Calif.) to enable sellers to author and manage listings on the networked system 102 in an off-line manner, and to perform batch-mode communications between the programmatic client 116 and the networked system 102.

Figure 2A:
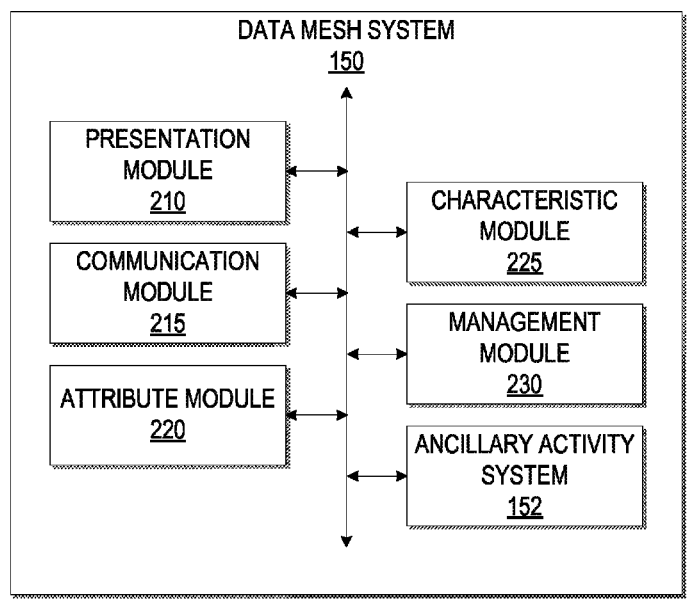
FIG. 2A is a block, diagram illustrating an example embodiment of a data mesh system, according to some example embodiments.
Figure 2B:
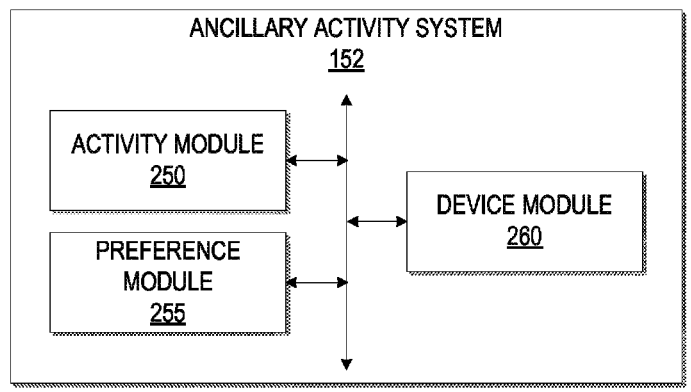
FIG. 2B is a block diagram illustrating an example embodiment of an ancillary activity system, according to some example embodiments.

FIG. 2A is a block diagram of the data mesh system 150, which can provide functionality to receive, retrieve, or access attribute data from attribute sources, analyze the attribute data, manage the attribute data, and so forth. In an example embodiment, the data mesh system 150 can include a presentation module 210, a communication module 215, an attribute module 220, a characteristic module 225, a management module 230, and the ancillary activity system 152. FIG. 2B is a block diagram of the ancillary activity system 152, which can provide functionality to generate ancillary activities based on various triggers and information. The ancillary activity system 152 includes an activity module 250, a preference module 255, and a device module 260, according to an example embodiment. All, or some, of the modules 210-260 of FIGS. 2A and 2B, can communicate with each other, for example, via a network coupling, shared memory, and the like. It will be appreciated that each module of modules 210-260 can be implemented as a single module, combined into other modules, or further subdivided into multiple modules. It will further be appreciated that in some embodiments the modules or functionality of the ancillary activity system 152 is implemented in the data mesh system 150 and the modules or functionality of the data mesh system 150 is implemented in the ancillary activity system 152. Other modules not pertinent to example embodiments can also be included, but are not shown.

Referring to FIG. 2A, the presentation module 210 provides various presentation and user interface functionality operable to interactively present and receive information from users. For example, the presentation module 210 causes presentation of various notifications or user interfaces that provide the user an option to make a purchase associated with the identified items. The presentation module 210 presents or cause presentation of information using a variety of means including visually displaying information and using other device outputs e.g., acoustic, haptic). Interactively presenting is intended to include the exchange of information between a device and a user. The user can provide input to interact with the user interface in a variety of ways including alphanumeric input, cursor input, tactile input, or other input (e.g., one or more touch screen, camera, tactile sensors, light sensors, infrared sensors, biometric sensors, microphone, gyroscope, accelerometer, or other sensors). It will be appreciated that the presentation module 210 provides many other user interfaces to facilitate functionality described herein. Further, it will be appreciated that "presenting" as used herein is intended to include communicating information to another device with functionality operable to perform presentation using the communicated information.

The communication module 215 provides various communications functionality and web services. For example, the communication module 215 provides network communication such as communicating with the networked system 102, the client device 110, and the third party server(s) 130. In various example embodiments, the network communication operates over wired or wireless modalities. Web services are intended to include retrieving information from the third party server(s) 130, the database(s) 126, and the application server(s) 140. Information retrieved by the communication module 215 comprises data associated with the user (e.g., user profile information from an online account, social network service data associated with the user), data associated with one or more items listed on an e-commerce website (e.g., images of the item, reviews of the item, item price), other data to facilitate the functionality described herein, and so on.

The attribute module 220 can receive, access, or retrieve a wide variety of attribute data from many different attribute sources. For example, the attribute module 220 receives, retrieves, or accesses the attribute data from user devices or machines (e.g., the client device 110), social network services, the third party server(s) 130, the publication system(s) 142, the payment system(s) 144, other applications servers, or other attribute sources. The attribute data, as used herein, is intended to include raw data such as sensor data, profile data, social network content, and so on.

In some example embodiments, the attribute module 220 extracts the attribute data from various sources. For instance, a payment history log of the user can include a tremendous amount of extraneous data. The attribute module 220 can extract purchase information such as item purchased, time, purchase price, seller, location, brand, and so forth from the payment history log of the user.

In further example embodiments, the attribute module 220 performs various functions to prepare or condition the attribute data for analysis. For instance, the attribute module 220 standardizes the attribute data to facilitate analysis of the attribute data (e.g., determine a normal form for the data to allow for comparison and other mathematical analysis). The attribute module 220 performs many other functions to prepare the attribute data for analysis.

In various example embodiments, the attribute module 220 stores the attribute data in association with the user for subsequent analysis. For example, the attribute module 220 stores the attribute data in the database(s) 126. The attribute data can be stored in conjunction with a user identifier such that the attribute module 220 subsequently uses the user identifier to access the attribute data corresponding to a particular user. The attribute module 220 accesses the stored attribute data using other schemes. For instance, the attribute module 220 accesses a portion of the attribute data associated with a time, an item, a user, a type of user, a particular attribute source, and so forth. In this way, the attribute module 220 accesses a portion of attribute data according to various parameters from among a large quantity of the attribute data to access, identify, or find pertinent and relevant data.

The characteristic module 225 infers a user characteristic or multiple user characteristics corresponding to the user based on an analysis of at least a portion of the attribute data. Many schemes and techniques can be employed to infer the characteristic from the attribute data. For example, a particular user characteristic can be a work location of the user. The attribute data can include a plurality of locations e.g., as determined by a GPS component of a user device used by the user) that include time stamps. The work location of the user can be inferred based on the consistency and timing of the locations included in the attribute data (e.g., during normal working hours, the user is typically at a particular office building). Many different portions of attribute data and combinations of portions of attribute data can be analyzed to infer a wide variety of characteristics.

In various example embodiments, characteristics (e.g., the user characteristics), as used herein, are intended to include traits, qualities, actions, activities, attitudes, habits, behaviors, and the like pertaining to a person or people. Inasmuch as the attribute data may not necessarily pertain to a person (e.g., raw data such as coordinates of a particular location), a characteristic (e.g., current location of the user, disliking spicy food, having young children, being a Star Trek fanatic) can be distinct from the attribute data.

The management module 230 provides management functions associated with the attribute data. For example, the management module 230 provides the user with functionality to edit, modify, update, or otherwise control the attribute data. For instance, the user removes undesired attribute data via the functionality provided by the management module 230. In a further instance, the user specifies permissions for portions of the attribute data using the functionality provided by the management module 230. The permissions allow or prohibit certain access or uses for the attribute data (e.g., the permission prohibits access to the attribute data by third parties). Various levels of access and abilities can be granted. In some example embodiments, the permissions persist for a period of time, and after expiration of the time period, the permissions are revoked.

In further example embodiments, the management module 230 requests consent from the user to access portions of the attribute data or to request permission for certain uses of the attribute data. For example, the management module 230 requests consent from the user to allow third parties to access portions of the attribute data. The management module 230 requests a variety of other consents associated with various actions corresponding to the attribute data.

In still further example embodiments, the management module 230 provides functionality to allow third parties to access the attribute data or user characteristics. For example, the management module 230 provides a set of APIs that can be invoked by third parties to access the attribute data or user characteristics. As discussed above, in some example embodiments, permission or consent of the user is determined prior to providing access to the attribute data.

Referring now to FIG. 2B, the activity module 250 in the ancillary activity system 152 provides functionality to generate the ancillary, supplemental, complementary, or companion activity corresponding to the device activity. For example, the user can be browsing a website and the activity module 250 generates the ancillary activity comprising providing the user interactive content such as an option to share, like, post (e.g., tweet), and so forth the website. The activity module 250 generates many other ancillary activities corresponding to the device activity based on various triggers and information.

The preference module 255 provides functionality to infer a user preference, from the attribute data, indicating a preference of the user associated with performing on the secondary user device the ancillary activity corresponding to the device activity. For example, the preference module 255 infers that the user desires or prefers a particular type of content associated with a particular device activity. The preference module 255 also identifies other users that are similar to the user and infer the user preference based on the identified similar users. The preference module 255 employs a variety of schemes and techniques using a wide range of data to infer the user preference.

The device module 260 provides functionality to identify the secondary user device according to a device status of the secondary user device. In various implementations, the device status indicates a device capability to perform the ancillary activity in real-time. The device module 260 retrieves, derives, determines, or otherwise obtains a variety of information associated with the user device and the secondary user device to facilitate the functionality herein. For example, the device module 260 determines available functionality of the secondary user device.

Figure 3:
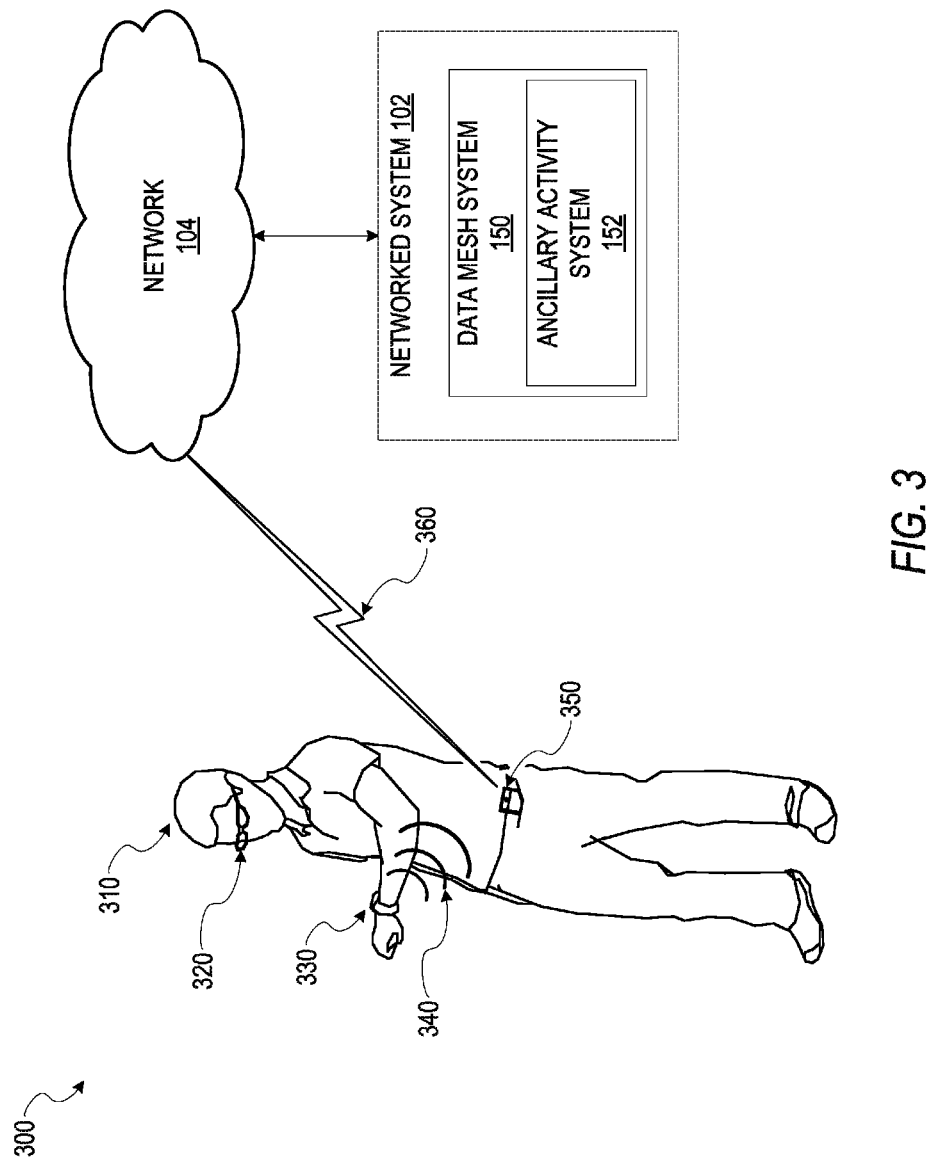
FIG. 3 illustrates an example of generating ancillary activity for a secondary user device, according to some example embodiments.

FIG. 3 illustrates a diagram 300 showing an example of generating ancillary activity for a secondary user device, according to some example embodiments. User 310 may be using wearable computing devices such as wearable device 320 (e.g., Google Glass®) or wearable device 330 (e.g., a smart watch). In this example, the wearable device 330 is communicatively to user device 350 via wireless signals such as signal 340. In various implementations, the user device 350 is communicatively coupled, via coupling 360, to the network 104, which is in turn communicatively coupled to the networked system 102 including the data mesh system 150 (discussed above in connection with FIG. 2A) and the ancillary activity system 152 (discussed above in connection with FIG. 2B).

The user 310 may be operating or using the user device 350. The terms "operating," "using," "in service," or "in use" as used herein are intended to include a particular user physically interacting with a particular device, being capable of operating the particular device within a short time period such as dormant device or a device in standby (e.g., a particular user carrying a mobile device on their person without present physically interaction is included in the terms "operating," "using," or "in use"), or otherwise utilizing the particular device (e.g., a smart refrigerator, that is not within a vicinity of the user, configured to track inventory levels and provide inventory data).

In the example diagram 300, the user 310 is carrying the user device 350 that is communicatively coupled to the ancillary activity system 152. The activity module 250 detects the device activity of the user device 350. For instance, the user 310 can be browsing a webpage, receiving directions to a particular location, monitoring fitness activity such as a number of steps taken, and so forth using the user device 350.

Once the activity module 250 detects the device activity, the preference module 255 infers the user preference from the attribute data accessed by the attribute module 220. The user preference indicates a preference of the user or desire of the user for performing, on a particular user device, a particular ancillary activity corresponding to the device activity. For example, the preference module 255 infers that the user 310 would like an option, presented on a particular wearable device, to favorite, share, post (e.g., tweet) associated with a webpage the user 310 is browsing on the device 350.

Based on the inferred user preference, the device module 260 identifies the secondary user device according to the device status of the secondary user device. The device status indicates that the device is capable of performing the ancillary activity. For example, the device module 260 identifies the wearable device 330 as the secondary user device based on the device status corresponding to the wearable device 330. In this example, the device module 260 determines the device status of the wearable device 330 as being in use by the user 310 (e.g., the user 310 wearing the wearable device 330). Thus, the wearable device 330 is operable to perform the ancillary activity since providing the option for the user 310 to select can be effectuated by the wearable device 330 as the user 310 is within an operating distance of the wearable device 330.

After the device module 260 identifies the secondary user device, the activity module 250 generates the ancillary activity to be performed in real-time on the secondary user device. The activity module 250 generates the ancillary activity by analyzing the device activity, a device functionality of the secondary user device, the user preference, and other data. The device functionality indicates options available for input and output on the secondary user device. For example, the identified secondary user device is the wearable device 330 that has a small screen area to display user interfaces or has reduced options for output (e.g., no speakers). In a specific instance, the activity module 250 generates the ancillary activity to include abridged activity content according to the device functionality (e.g., small display size). After the activity module 250 generates the ancillary activity, the activity module 250 transmits or otherwise communicates to the secondary user device to perform the ancillary activity in real-time.

Figure 4:
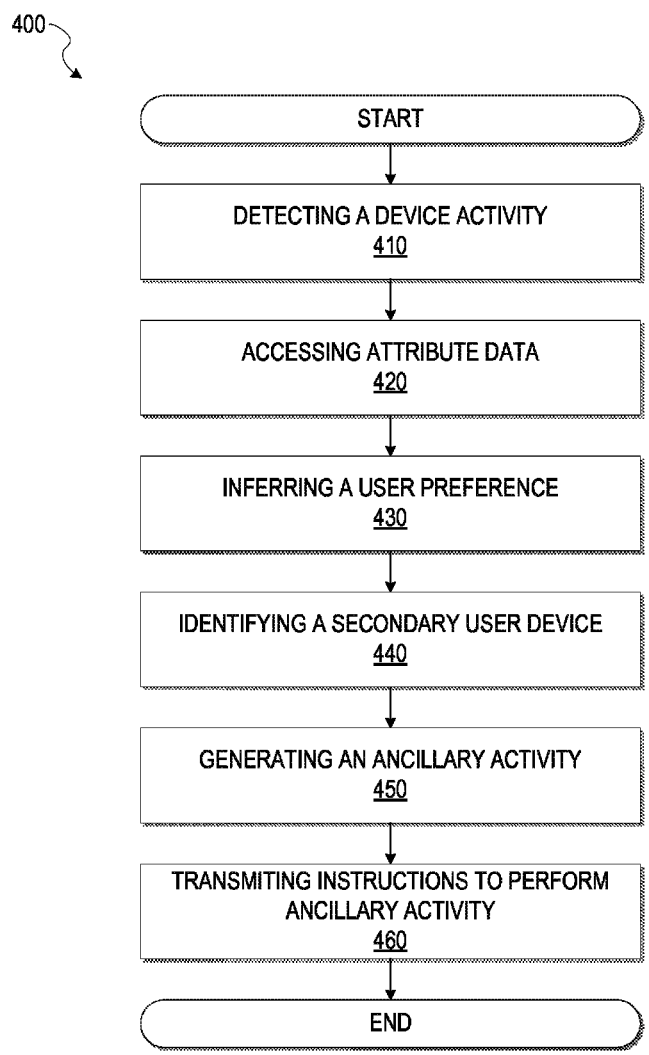
FIG. 4 is a flow diagram illustrating an example method for generating ancillary activity for a secondary user device, according to some example embodiments.

FIG. 4 is a flow diagram illustrating an example method 400 for generating ancillary activity for the secondary user device, according to some example embodiments. At operation 410, the activity module 250 detects the device activity being performed in real-time by the user device of a user.

The term "real-time data," as used herein, is intended to include data associated with an event currently happening. For example, the device activity being performed in real-time includes a particular device activity detected at the activity module 250 after a delay interval (e.g., due to transmission delay or other delays such as being temporarily stored at an intermediate device) between the instant of the particular device activity occurring and the activity module 250 detecting the particular device activity. Thus, in some instances, the device activity being performed in real-time is intended to include activities that have occurred a short time in the past. This discussion of real-time applies equally throughout the specification in relation to other uses of the term "real-time."

In various embodiments, the device activity includes a wide variety of activities such as browsing a webpage, monitoring fitness activity (e.g., steps the user has taken), heart rate monitoring, inventory level monitoring (e.g., a smart refrigerator that monitors inventory), and so on. In some implementations, the activity module 250 detects the device activity being performed by monitoring devices of the user. For instance, a smart appliance of the user provides a continuous or periodic stream of data indicating various device activities.

At operation 420, the attribute module 220 accesses the attribute data associated with the user from the plurality of attribute sources. In various example embodiments, at least a portion of the attribute data includes real-time data or near real-time data. For example, the real-time data includes user input data or sensor data communicated to the attribute module 220 after a delay interval (e.g., due to transmission delay or other delays such as being temporarily stored at an intermediate device) between capturing the data and the attribute module 220 receiving the data.

As will be discussed in connection with FIGS. 14 and 15, the attribute data is received from a broad spectrum of attribute sources (e.g., devices, sensors, servers, databases, and other sources). Additionally, the attribute module 220 receives or accesses the attribute data via many pathways resulting from an assortment of configurations of the attribute sources as further discussed in connection with FIGS. 13A and 13B. In an example embodiment, the attribute module 220 receives the attribute data directly from the attribute sources. In other example embodiments, the attribute module 220 receives the attribute data from a central device that receives attribute data from a plurality of user devices. In still other example embodiments, various user devices are communicatively coupled in a decentralized device-to-device mesh, and the attribute module 220 receives the attribute data corresponding to a particular device in the mesh from any of the devices in the mesh. The attribute module 220 receives the attribute data from the attribute sources in many other configurations including various suitable combinations of configurations.

In various example embodiments, the attribute module 220 stores the attribute data in association with the user (e.g., indexed based on a user identifier) for subsequent analysis. The attribute module 220 stores the attribute data in a storage device such as the database(s) 126, for example. The attribute module 220 accesses the stored attribute data using a variety of search or find schemes. For instance, the attribute data associated with a particular user is accessed using a user identifier that corresponds to the particular user. It will be noted that the collective, aggregated attribute data is sometimes referred to as a "data mesh."

At operation 430, the preference module 255 infers the user preference or desired user setting, from the attribute data, indicating a preference of the user for performing on the secondary user device the ancillary activity corresponding to the device activity. For example, the attribute data includes engagement data of the user (e.g., particular websites the user visits, taps, clicks, or other interactions with various notification) indicative of the types of information the user is interested in. In a specific example, the preference module 255 infers the user preference for receiving notifications associated with a particular sporting event based on the engagement data.

In this specific example, the activity module 250 detects from the user device (e.g., a smart television) that the device activity includes watching a sporting event. In continuing with this example, the preference module 255 infers the user preference to indicate the user has an affinity for notification associated with watching a sporting event on a particular secondary device based on past notifications the user showed interest in that are included in the attribute data.

Figure 5:
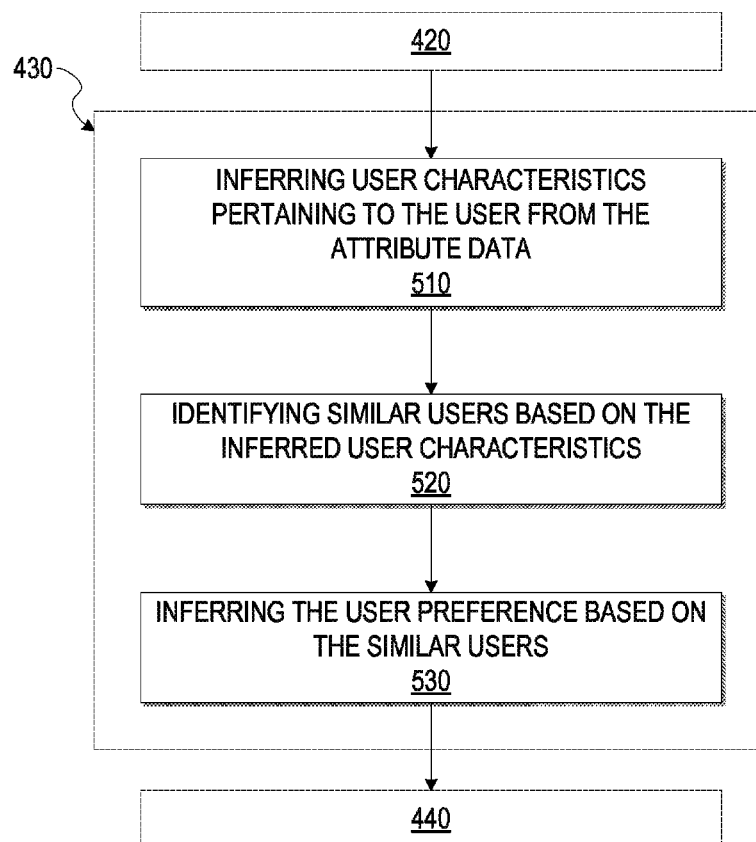
FIG. 5 is a flow diagram illustrating further operations for inferring a user preference from the attribute data, according to some example embodiments.

Referring now to FIG. 5, a flow diagram is shown illustrating further operations for inferring a user preference from the attribute data, according to some example embodiments. As discussed above, subsequent to the operation 420, at the operation 430, the preference module 255 infers the user preference from the attribute data.

At operation 510, the characteristic module 225 infers or directly measures user characteristics pertaining to the user from the attribute data. In some example embodiments, the characteristic module 225 stores the inferred user characteristics for subsequent analysis, for example, in a storage device such as database(s) 126. The characteristic module 225 infers a vast spectrum of the user characteristics from the attribute data. A few specific examples of user characteristics include demographic data (e.g., age, gender, marital status, number of children), user preferences (e.g., being a morning person, favorite locations, enjoying spicy food), idiosyncrasy (e.g., being forgetful, such as draining the battery on a mobile device; or being impatient, such as a line breaker that will leave a store if the line is too long), qualities (e.g., being athletic, being tall, having a large vocabulary), personality traits (e.g., being a risk taker), actions, activities (e.g., working for a non-profit), attitudes, habits (e.g., being a coffee drinker), behaviors, beliefs, biases, demeanor, and physical characteristics of the user e.g., height, weight, garment sizes, eye color, hair color). The specificity of the characteristics ranges from very narrow (e.g., drinks a particular brand of soda) to very broad (e.g., being generally philanthropic). To illustrate inferring the user characteristic from the attribute data in an example, the attribute data includes user location data that indicates frequent visits to a local school, local soccer fields, and the like. In this example, the characteristic module 25 infers that the user has children based on the types of locations the user may be frequently visiting.

In some instances, the characteristic module 225 performs varying degrees of inferential analysis of the attribute data to derive the user characteristics. For example, the characteristic module 225 infers the user's wake-up time based on user device activity or other activity (e.g., connected alarm clock settings, logins to accounts, and various other user activities that indicate a wake-up time). In this example, the characteristic module 225 infers a particular user characteristic that can be of a larger inferential jump such as the user being a morning person or a person that likes to sleep in. The degree of inferential jump can be configurable. In some example embodiments, the characteristic module 225 employs various techniques to minimize or otherwise control incorrect inferences (e.g., machine-learning, other learning algorithms).

In further example embodiments, the characteristic module 225 learns, adapts, or evolves as more of the attribute data is received (e.g., via machine learning techniques or other learning algorithms). For example, the attribute data includes location data of the user. The characteristic module 225 infers a favorite location of the user based on a pattern (e.g., frequently visited locations) in the location data. However, the characteristic module 225 subsequently receives employment data of the user that indicates a current employer including an employer location. The characteristic module 225 learns, updates, or otherwise adapts to account for the new attribute data. Thus, in this example, the characteristic module 225 may not infer a favorite location of the user if the location is a work location of the user. In some instance, the user may provide input directly (e.g., via a user interface configured to receive inferential guidance from the user) to facilitate the characteristic module 225 in inferring characteristics from the attribute data (e.g., user input indicating that a particular inferred characteristic is incorrect or providing input to be used as a basis for future inferences).

In other instances, the characteristic module 225 performs very little or no analysis to derive the user characteristic from the attribute data. For example, the attribute data includes an alarm time setting from a connected alarm clock (e.g., a smart phone with an alarm clock app). The alarm time setting can directly indicate a wake-up time. Since the attribute data directly relates to a particular user characteristic, the characteristic module 225 need not perform analysis to derive the user characteristic.

In some example embodiments, the user characteristic comprises predefined characteristics or dynamically determined characteristics. For instance, a particular set of characteristics is predefined (e.g., work location, home location, marital status, socio-economic level). In this instance, the characteristic module 225 determines that particular predefined characteristics are associated with the user based on an analysis of the attribute data. In other instances, the characteristic module 225 dynamically determines characteristics based on the attribute data. For example, the attribute data indicates that the user owns a particular exotic pet. Although there may not be a predefined characteristic associated with the particular exotic pet, the characteristic module 225 determines the user characteristic of owning an exotic pet from the attribute data.

At operation 529, the preference module 255 identifies similar users that are similar to the user based on the inferred user characteristics and respective user characteristics of a plurality of other users. The preference module 255 identifies similar users that are similar to the user based on a variety of factors. In some example embodiments, the preference module 255 accesses the attribute data or stored user characteristics corresponding to the plurality of other users. For example, the preference module 255 identifies the similar users from among the plurality of other users that are similar to the user based on the inferred user characteristics of the user and respective user characteristics of the plurality of other users. The preference module 255 correlates, matches, or otherwise compares the inferred user characteristics with respective user characteristics of the plurality of other users to identify the similar users. In various example embodiments, the preference module 255 identifies the similar users based on same or similar demographic data (e.g., same or similar age, marital status, gender, geographic location, etc.), same or similar user characteristics (e.g., same or similar brand purchases), same or similar attribute data, and so on.

At operation 530, the preference module 255 infers the user preference or desired user setting based on the identified similar users. For example, the preference module 255 analyzes the user characteristics of the identified similar users to determine the user preference. In a specific example, if the user characteristics of the identified similar users indicate a preference for viewing particular content on a particular secondary user device, the preference module 255 infers that the user also has the same or a similar preference tier viewing the particular content on the particular secondary user device. In this way, the preference module 255 infers the user preference based on the identified similar users.

Referring back to FIG. 4, at operation 440, the device module 260 identifies the secondary user device according to the device status of the secondary user device. The device status indicates a device capability to perform the ancillary activity in real-time. The device capability includes various metrics and features associated with the secondary user device. In various implementations, the device module 260 identifies the secondary user device based on the device status that includes various combinations of factors discussed below. For example, the device status can be based on the device capability including a distance of the secondary user device to the user as further discussed in connection with FIG. 6, below. For instance, the secondary user device is capable of presenting information or notification to the user if the secondary user device is within a vicinity of the user.

In another example, the device status is based on a particular functionality of the device. The device module 260 queries the secondary user device to determine the functionality of the secondary user device. In other instance, the device module 260 determines the functionality of the secondary user device via a lookup of functionality for the same or similar device as the secondary user device. For instance, if the secondary user device is a particular type of wearable device, the device module 260 can lookup available functions for the particular type of wearable device from the third party servers(s) 130. For instance, if the secondary user device has an audio output, then the device module 260 identifies the secondary user device as capable of performing a particular ancillary activity that includes audio output (e.g., voice directions for hands free navigation). Thus, in some cases, the device module 260 determines the device status in conjunction with a particular ancillary activity.

In still another example, the device status is based on whether the secondary user device is active as further discussed in connection with FIG. 7, below. For example, if the secondary user device is not currently being used (e.g., as determined via a sensor on the device such as an accelerometer that indicates the device is perfectly still), then the device module 260 determines that the device is not active and does not identify the inactive secondary user device as being capable of performing the ancillary activity.

Referring now to FIG. 6, a flow diagram illustrates further operations for identifying a secondary user device, according to some example embodiments. Specifically, FIG. 6 is directed to the device module 260 identifying the secondary user device by determining that the device status of the secondary user device includes the secondary user being within a distance of the user. Subsequent to the operation 430, the device module 260 receives sensor data from the secondary user device at operation 610. The sensor data includes, for example, data received from any of the sensors discussed in connection with FIG. 15, below. In a specific example, the sensor data includes location data as determined by a GPS component of the secondary user device. The sensor data represents a real-time physical environment of the secondary user device. As discussed below, the device module 260 determines the device status of the secondary user device based on the sensor data received from the secondary user device.

At operation 620, the characteristic module 225 or the device module 260 infers the current user location based on location data received from the user device. For example, the attribute data includes real-time data, from the user device, corresponding to the location of the user (e.g., location data as determined by a GPS component of a mobile device corresponding to the user).

At operation 630, the device module 260 extracts a current device location from the sensor data received from the secondary user device. For instance, the secondary user device can be equipped with a GPS component that provides location data. In other instances, the device module 260 extracts the current device location based on Wi-Fi® triangulation, NFC beacon detection, or other location services.

At operation 640, the device module 260 compares the current user location and the current device location to determine that the secondary user device is within a distance (e.g., an operating distance of the current user location. The distance may be a short distance such as a reasonable distance to allow the user to physically operate the secondary user device (e.g., an arm's length).

Although FIG. 6 is directed to determining that the secondary user device is within a distance of the user location based on an inferred location of the user and the secondary user device, the device module 260 employs other schemes to determine whether the user is within an operating distance of the secondary user device. For instance, if the secondary user device is equipped with biometric identification sensors and the device module 260 receives biometric sensor data from the secondary user device indicating the identity of the user, the device module 260 can, in that situation, infer that the user is within an operating distance of the secondary user device.

Referring now to FIG. 7, a flow diagram illustrates further operations for identifying the secondary user device, according to some example embodiments. Subsequent to the operation 430, the device module 260 receives sensor data from the secondary user device at operation 710, similar to the operation 610 described above. The sensor data represents a real-time physical environment of the secondary user device. For instance, the sensor data includes thermal data (e.g., data that indicates a current temperature), motion data (e.g., as determined by an accelerometer component), position data (e.g., as determined by a GPS component), biometric data (e.g., heart rate data or fingerprint identifications), communication data (e.g., NFC beacon detections or Bluetooth® device detections), and other sensor data (see FIG. 15 below for additional sensors and data).

At operation 729, the device module 269 calculates an active metric from the sensor data. In various implementations, the active metric indicates the secondary user device is in use by the user. In some implementations, the active metric comprises a probability or likelihood that the secondary user device is active. In these implementations, a higher value for the active metric is associated with a higher probability that the secondary user device is active. In a specific instance, if the secondary user device is a wearable device such as a smart watch, the sensor data indicates that a particular user is wearing the wearable device based on a heart rate sensor (when the user is not wearing the wearable device the heart rate sensor indicates no heart rate).

Similarly, if the secondary user device is a smart phone that provides ambient temperature data, the device module 260 calculates the active metric based on the temperature data. For example, if the temperature data is fluctuating or is above an expected ambient temperature, this indicates that the user is carrying the smart phone in their pocket. Conversely if the temperature is near expected ambient temperature and there is little fluctuation in the temperature, the device module 260 calculates a low probability, corresponding to a lower active metric, indicating that the particular device is not active or in use by the user.

At operation 739, the device module 269 determines that the secondary user device is active based on the active metric. For example if the calculated active metric exceeds a threshold value, the device module 260 deter nines that the secondary user device is active. The threshold value can be predetermined or dynamically determined by the device module 260. For example, the device module 260 employs various statistical models based on historical values of the active metric to determine whether the current active metric is anomalous. In a simple non-limiting example, the device module 260 determines the threshold value to be an average of historical values for the active metric, and the device module 260 determines that the secondary user device is active if the active metric exceeds the average of the historical values of the active metric. The device module 260 employs many other schemes and techniques to determine that the device is active based on the active metric.

At operation 740, the device module 260 identifies the secondary user device as being capable of performing the ancillary activity in real-time based on the secondary user device being active. That is to say, the device module 260 identifies a particular secondary user device based on the particular secondary user device being active. The reasoning being that if the secondary user device is inactive, the secondary user device is not capable of presenting information to or receiving input from the user and therefore is not capable of performing the ancillary activity, in some cases.

Referring again to FIG. 4, at operation 450, the activity module 250 generates the ancillary activity, to be performed in real-time on the secondary user device, by analyzing the device activity, a device functionality of the secondary user device, the user preference, and other factors and data. The ancillary activity can include a wide range of tasks, content, and functionality. For example, the ancillary activity comprises a notification that includes notification content associated with the device activity. For instance, if the device activity is viewing a sporting event on a smart TV, the ancillary activity comprises a notification including notification content associated with the sporting event (e.g., information about the players, the current score, sporting statistics).

In some implementations, the ancillary activity includes a portion of the device activity. For example, if the device activity comprises browsing a particular website, the activity module 250 generates the ancillary activity to include content that is a portion of the website. Thus, in these implementations, the activity module 250 is distributing a portion of the device activity to the secondary user device.

FIG. 8 is a flow diagram illustrating further operations for generating the ancillary activity of the secondary user device, according to some example embodiments. Subsequent to the operation 440, at the operation 450, the activity module 250 generates the ancillary activity. The operation 450 can further include operations 810, 820, and 830.

At operation 810, the device module 260 determines a display size corresponding to the secondary user device. For example, the device module 260 queries the secondary user device directly to retrieve data associated with the display size. In another example, the device module 260 queries a particular third party server (e.g., the third party server(s) 130) using an identifier associated with the secondary user device to determine the display size of the secondary user device. In a specific example, the device module 260 determines a particular device model for the secondary user device and performs a lookup of the display size for the particular device model.

At operation 820, the device module 260 determines the display size corresponding to the secondary user device is below a threshold size. For example, the display size may be too small for particular content of the ancillary activity. In this situation, the device module 260 determines that the display size is below the threshold size.

At operation 830 the activity module 250 generates the ancillary activity to include abridged activity context according to the display size corresponding to the secondary user device. For instance, the device module 260 shortens or reduces content or functionality of the ancillary activity to accommodate the display size of the secondary user device.

FIG. 9 is a flow diagram illustrating further operations for generating the ancillary activity of the secondary user device, according to some example embodiments. Subsequent to the operation 440, at the operation 450, the activity module 250 generates the ancillary activity. The operation 450 further includes operations 910 and 920.

At operation 910, the device module 260 compares the device functionality of the secondary user device with a device functionality of the user device to identify non-mutual functionality of the secondary user device that is not available on the user device. For example, the user device comprises a mobile computer that the user is browsing a website on. The secondary user device can be a wearable device affixed to the user. In this example, the device module 260 identifies haptic output, for instance, of the secondary user device as being non-mutual functionality as the mobile computer may not have haptic output functionality. In another example, a particular wearable device may not include a GPS component while a smart phone device of the user may include a GPS component to determine current location. In this example, the device module 260 identifies use of the GPS component as non-mutual functionality.

At operation 920, the activity module 250 generates the ancillary activity to include an activity component that utilizes the non-mutual functionality of the secondary user device. In the examples discussed above, if the device module 260 determines that the secondary user device includes a GPS component while the user device does not include a GPS component, the activity module 250 utilizes location data from the secondary user device in generating the ancillary activity. In a specific example, if the user is browsing a particular webpage associated with a particular merchant or location, the activity module 250 generates the ancillary activity to include mapping directions to the particular location using the GPS component of the secondary user device to access the user's current location. Thus, the activity module 250 receives the particular location from the user device and communicates, to the secondary user device, the location and instructions to map directions to that location from the current location.

Turning again to FIG. 4, at operation 460, the activity module 250 transmits or otherwise communicates, to the secondary user device, instructions to perform in real-time the complementary activity. For example, the activity module 250 communicates instructions to the secondary user device to present a user interface that facilitates or effectuates the ancillary activity (e.g., a user interface including functionality to carry out the ancillary activity). In a specific example, if the ancillary activity comprises a notification including notification content, the activity module 250 transmits the notification including the notification content to the secondary user device to be presented to the user. Thus, in this example, the activity module 250 caused presentation of the notification on the secondary user device.

Although the operations 440-460 are directed to performing a single ancillary activity on a single secondary user device, other embodiments include identifying multiple secondary devices and generating multiple ancillary activities to be performed in real-time on one or more of the identified secondary user devices. For example, if the user is carrying a smart watch and wearing smart glasses, the generated ancillary activities can be distributed among the identified ancillary activities. For instance, haptic-based notifications can be directed to the user's smart watch while visual notification is directed to the user's smart glasses. 111 this instance, the activity module 250 distributes the multiple ancillary activities among the multiple secondary user devices based on respective device functionalities of the multiple secondary user devices. The activity module 250 employs other factors to distribute the multiple ancillary activities such as the user preference.

Figure 10:
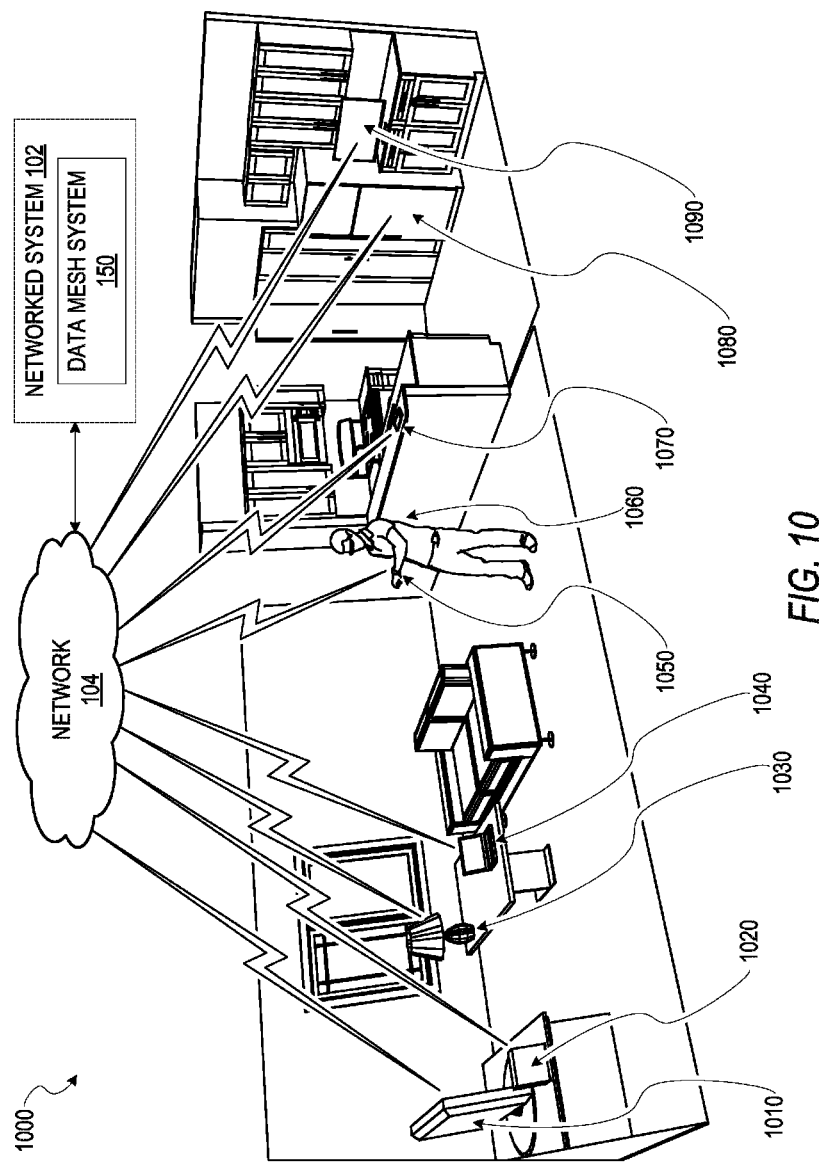
FIG. 10 illustrates an example scene showing a presentation of ancillary activity to the user, according to some example embodiments.

To help illustrate the concepts described above, FIG. 10 illustrates examples of generating the ancillary activity for the secondary user device, according to some example embodiment. FIG. 10 includes a scene 1000 that depicts a living room attached to an open kitchen. The scene 1000 includes a smart television (TV) 1010, a media entertainment device 1020, a lamp 1030, a mobile computer 1040, a wearable device 1050, a user 1060, a mobile device 1070, a smart refrigerator 1080, and a kitchen display 1090. Each of the devices of FIG. 10 can be attribute sources coupled to a network (e.g., the network 104) and operable to communicate with the data mesh system 150. In various example embodiments, the user 1060 may be carrying or wearing a smart device such as the wearable device 1050 (e.g., a mobile device, a wearable device, a NFC enable smart ring) on their person that provides real-time data corresponding to the user 1060. For instance, the user 1060 may be carrying a mobile device that provides real-time location data (e.g., as determined by a GPS component, beacon location detect, or other location services).

In an example embodiment, the user 1060 may be browsing a webpage using the mobile computer 1040. The mobile computer 1040 can be coupled to the network 104 and the activity module 250 detects the device activity of browsing a particular webpage. The preference module 255 infers a user preference associated with the device activity of browsing a particular webpage. For instance, the activity module 250 infers that the user has a preference for viewing supplemental content associated with the particular webpage the user is browsing or supplemental functionality associated with the particular webpage (e.g., liking, favoriting, or sharing the particular webpage).

Based on the inferred user preference, the device module 260 identifies the secondary user device such as the wearable device 1050 that is capable of performing the ancillary activity. The device module 260 identifies the wearable device 1050 based on the wearable device 1050 being within an operating distance of the user 1060 (the reasoning being that if the wearable device 1050 is within a short distance of the user, then the wearable device 1050 is capable of providing information or receiving input from the user). For example, the device module 260 determines the user is wearing the wearable device 1050 based on various sensor data received from the wearable device 1050 (e.g., biometric data that indicates a particular user is wearing the device, accelerometer data that indicates the device is in use. Bluetooth® device detections that indicates the wearable device 1050 is within short range communication range of another user device that the device module 260 has inferred the user is using).

Once the device module 260 identifies the wearable device 1050, the activity module 250 generates the ancillary activity based on the device functionality of the identified secondary user device, the device activity, the user preference, and other data. For example, the wearable device 1050 may not have an audio output; in that case, content including an audio component can be altered or modified to accommodate the functionality of the wearable device 1050. In continuing with the example above, the activity module 250 generates the ancillary activity to include options to favorite, like, share (e.g., tweet) the particular webpage the user is browsing. In some instances, the activity module 250 generates the ancillary activity based on the device activity. For example, if the device activity of browsing a particular webpage already includes options to favorite or share the webpage, the activity module 250 generates the ancillary activity to include functionality not already available at the user device (the mobile computer 1040 in this case). After the activity module 250 generates the ancillary activity, the activity module 250 transmits or otherwise communicates to the wearable device 1050 to perform the ancillary activity. In this example, the activity module 250 transmits instructions to the wearable device 1050 to present a user interface including the options to favorite, like, or share the particular webpage the user is browsing on the mobile computer 1040.

EXAMPLE USER INTERFACES

Figure 11:
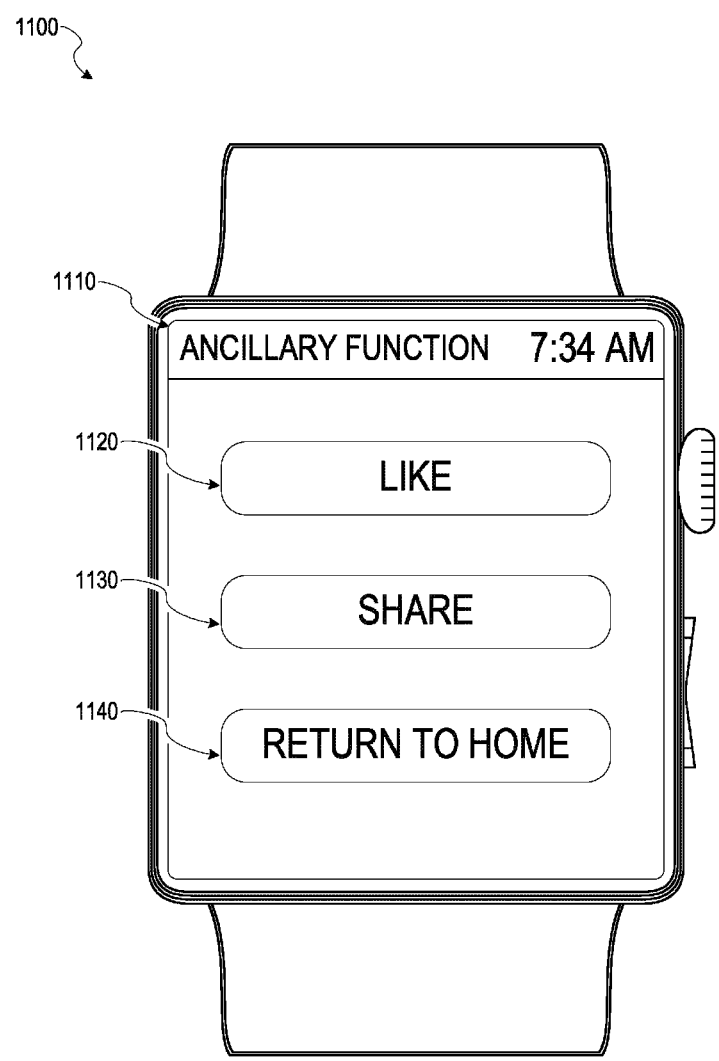
FIGS. 11 and 12 depict example user interfaces that present ancillary activity, according to some example embodiments.
Figure 12:
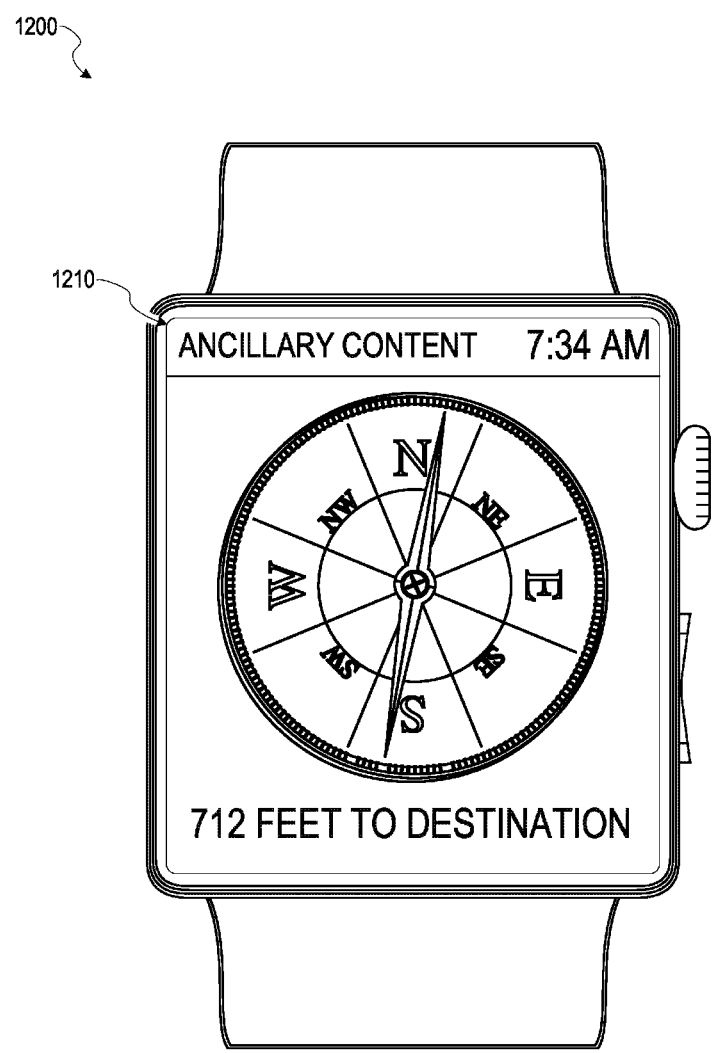

FIGS. 11 and 12 depict example user interfaces for interactively presenting information to the user. Although FIGS. 11 and 12 depict specific example user interfaces and user interface elements, these are merely non-limiting examples and many other alternate user interfaces and user interface elements can be generated by the presentation module 210 and presented to the user. It will be noted that alternate presentations of the displays of FIGS. 11 and 12 can include additional information, graphics, options, and so forth; other presentations include less information, or provide abridged information for easy use by the user.

FIG. 11 depicts an example device 1100 (e.g., smart watch) displaying an example user interface 1110 that includes ancillary or supplemental functionality. For example, the user interface 1110 includes user interfaces elements 1120, 1130, and 1140 that provide the user with options to like (e.g., like a particular webpage or a particular location), share (e.g., tweet a link to a particular location or a webpage), or return to home (e.g., navigate a particular webpage on the user device using the secondary user device) respectively. For example, activating the user interface element 1120 causes the secondary user device to "like" an item associated with the device activity (e.g., a particular webpage) on a social network service the user is a member of. The user interface 1110 includes a wide variety of other functionality.

In some cases, the ancillary activity comprises a notification. In these cases, the activity module 250 causes presentation of the notification to the user. For instance, the activity module 250 communicates, to the device 1100, instructions to present the notification. In some instances, the instructions include notification content, generated by the activity module 250, such as a message (e.g., pertinent information) to be presented to the user. In example embodiments, the notification comprises a text message, such as Short Message Service (SMS) messages, Multimedia Messaging Service (MMS), Enhanced Messaging Service (EMS), and so forth. In other example embodiments, the notification comprises a push notification or another similar type of notification. In further example embodiments, the notification comprises interactive user interface elements.

FIG. 12 depicts an example device 1200 displaying an example user interface 1210 that includes ancillary or supplemental content. For example, the user interface 1210 includes supplemental content associated with directions to a particular location. For instance, if the user is attempting to physically locate a particular place using a smart phone, the ancillary activity includes providing additional or supplemental content on a wearable device the user may be wearing. In the example of FIG. 12, the user interface 1210 includes a heading determined via sensors included in the wearable device or from data received from the smart phone. The supplemental content can also include pertinent information such as a distance to the specified location. In this way, the wearable device performs the ancillary activity associated with the device activity being performed in real-time by the user device of the user.

Figure 13A:
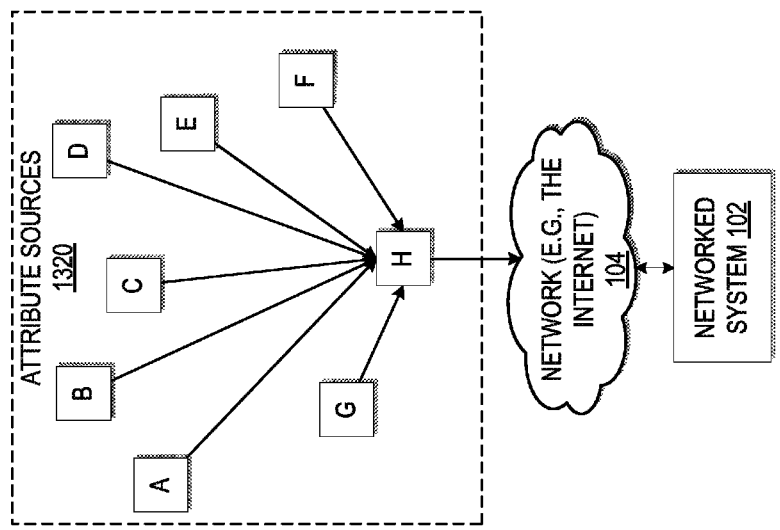
FIGS. 13A and 13B depict example configurations for communicatively coupling attribute sources, according to some example embodiments.
Figure 13B:
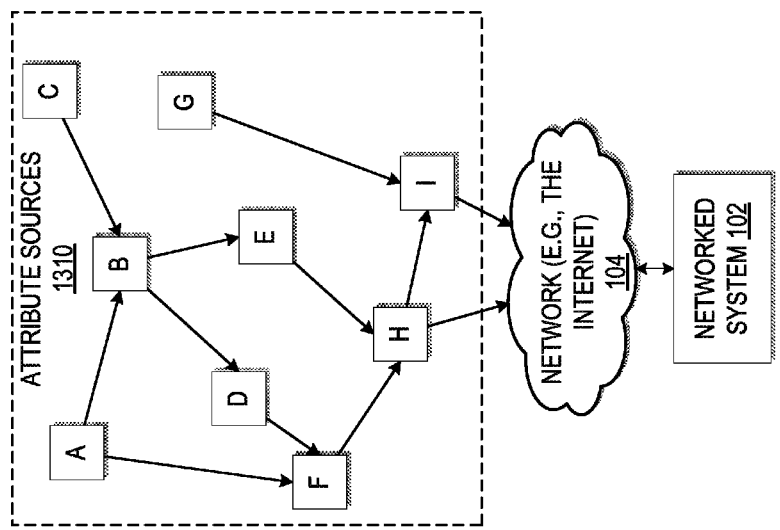

FIGS. 13A and 13B depict example configurations for communicatively coupling attribute sources, according to some example embodiments. The example embodiments described herein can access a vast and rich "Internet of Things" (IoT) dataset that is predominantly provided via connected, interconnected, or otherwise communicatively coupled machines and devices that can include a multitude of sensors. In example embodiments, devices and machines that provide the attribute data, such as the attribute sources, can be communicatively coupled in many different configurations. For instance, each attribute source is communicatively coupled to the networked system 102 independently to provide the networked system 102 access to the attribute data corresponding to each of the communicatively coupled attribute sources. FIGS. 13A and 13B depict alternative example attribute source configurations. It will be appreciated that FIGS. 13A and 13B are merely non-limiting examples of attribute source configurations and many other configurations or suitable combinations of configurations can be employed.

FIG. 13A depicts an example embodiment that includes attribute sources 1310 communicatively coupled in a decentralized device-to-device mesh. In this example embodiment, the attribute data corresponding to a particular device in the mesh may be received from any one or more of the devices in the mesh. For instance, the networked system 102 may access the attribute data corresponding to attribute source E via attribute source H or a combination of attribute sources H and I in FIG. 13A. In an example embodiment, the attribute source H or I may aggregate and store the attribute data corresponding to attribute sources A-F in FIG. 13A. In some example embodiments, the networked system 102 may access the attribute data associated with attribute source E by communicating with attribute source H or I in FIG. 13A.

FIG. 13B depicts another example embodiment that may include attribute sources 1320 communicatively coupled to a central attribute source (e.g., attribute source H in FIG. 13B). The networked system 102 may access the attribute data associated with attribute sources A-G via the central attribute source in FIG. 13B. In some embodiments, the central attribute source may aggregate and store the attribute data received or accessed from the attribute sources A-G and provide a centralized access point for the attribute data associated with all, or some, of the communicatively coupled attribute sources A-G in FIG. 13B.

Figure 14:
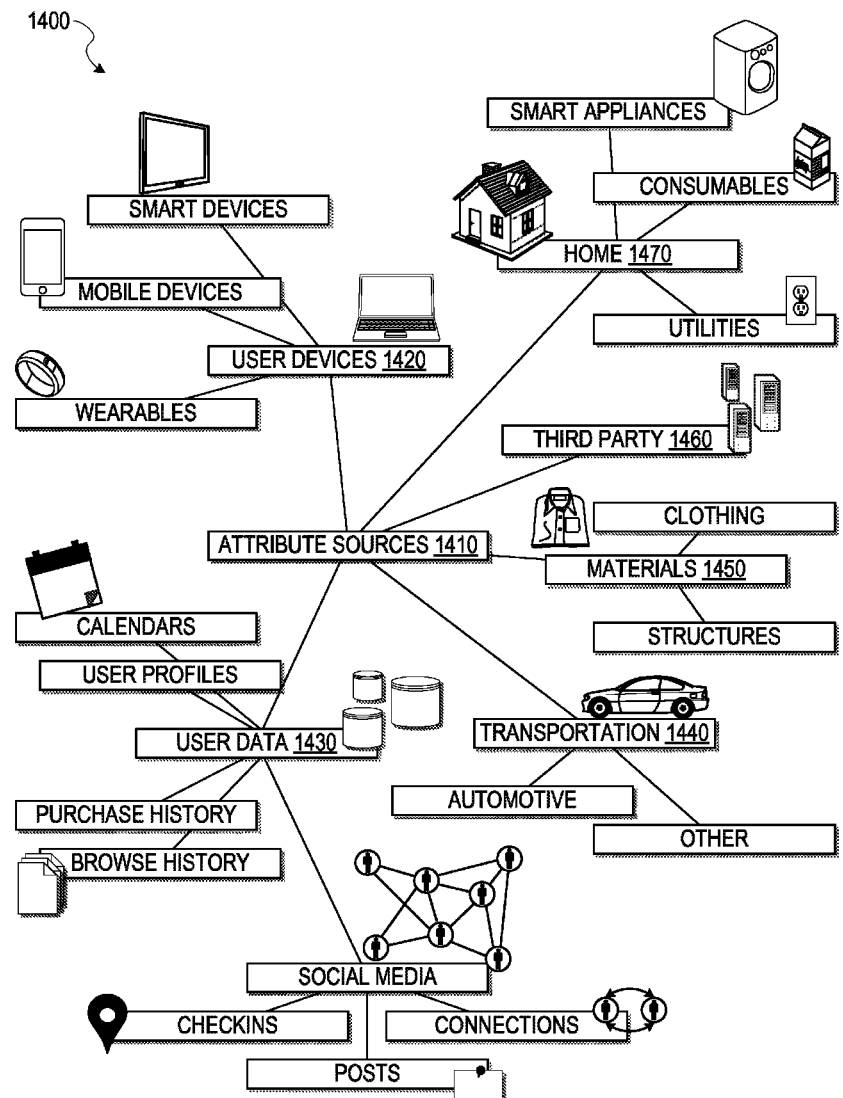
FIG. 14 depicts various example attribute sources, according to some example embodiments.

FIG. 14 depicts example sources 1400 including attribute sources 1410, according to some example embodiments. In various example embodiments, the attribute data may include data received, retrieved, or accessed from the attribute sources 1410. For example, the attribute sources 1410 may provide data including everything from a moisture level of a houseplant to a dribbling rhythm of a basketball. In some embodiments, the attribute data corresponding to the attribute sources 1410 may be received or accessed in real-time or near real-time. For instance, the attribute sources 1410 may communicate or otherwise provide access to the attribute data as it becomes available. In example embodiments, the attribute sources 1410 may include user device sources 1420, user data sources 1430, transportation sources 1440, materials sources 1450, third party sources 1460, home sources 1470, and a variety of other sources. As will be discussed in connection with FIG. 15, the attribute sources 1410 may be associated with a wide variety of sensors, gauges, measurement components, and other components.

In an example embodiment, the attribute data may include data corresponding to the user device sources 1420. The user device sources 1420 may include such non-limiting examples as a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), and other smart devices. As will be discussed further in connection with FIG. 15, the attribute data corresponding to the user device sources 1420 may include data associated with sensors, gauges, or other measurement components such as environmental sensor data (e.g., ambient temperature data associated with an environment of the user), biometric sensor data (e.g., heart rate data of the user), detection data (e.g., detection of a Near Field Communication (NFC) beacon), motion data (e.g., acceleration data), position data (e.g., location as determined by a GPS of a mobile device), and so forth.

In further example embodiments, the attribute data corresponding to the user device sources 1420 includes data such as device type, device model, device name, a unique device identifier, and other device parameters. In some example embodiments, the device type data provides a basis for an inference associated with the attribute data. For instance, if the device type data indicates that the device is a mobile device of the user, location data corresponding to the mobile device may indicate the location of the user. Similarly, if the device type is a media entertainment system, the attribute data corresponding to the media entertainment system may be associated with a home of the user.

The user data sources 1430 include, for example, calendars (e.g., user calendar events such as birthdays, trips, exams), user profiles (e.g., demographic information such as age, gender, income level), purchase histories, browse histories (e.g., search terms), social media content (e.g., check-ins, posts, connections), or other user data (e.g., bookmarked websites, preferences or settings for various applications, application usage data such as time spent using a particular application). The attribute data corresponding to the user data sources 1430 is stored, for example, by the user device sources 1420 (e.g., a mobile device that includes a mobile browser with browse history of the user), application server (s) 140 (e.g., payment history of the user stored in payment system(s) 144, user profiles stored by an e-commerce website), or the third party server(s) 130 (e.g., social media data stored in a social networking service). For instance, the attribute data corresponding to the user device sources 1420 includes device resource data. In some implementations, the device resource data includes files stored on the devices (e.g., digital media or apps) or metadata associated with the files (e.g., the number of time a particular song has been played or usage time corresponding to a particular app).

As cars and other forms of transportation become increasingly equipped with sensors and the ability to communicate, a vast amount of data may be provided by the transportation sources 1440. For example, the attribute data corresponding to the transportation sources 1440 may include acceleration data, velocity data, and other sensor data (e.g., brake pad wear data, gear shifting data, miles driven). In this example, the attribute data corresponding to the transportation sources 1440 may provide indications of a user's driving patterns and styles (e.g., comes to a complete stop at a stop sign, speeds, or finicky use of the brakes).

The materials sources 1450, such as clothing and structures, are also increasingly gaining the ability to capture data. In various example embodiments, the attribute data may include data corresponding to the materials sources 1450. For example, clothing may be embedded with sensors to detect motion. Data from these sensors may provide indications of whether the user is active or inactive. In another example, clothing may be embedded with biometric sensors that may provide a continuous feed of biometric data corresponding to the user. The biometric data may provide indications of the user's health, athletic ability, and many other characteristics corresponding to the user. Similarly, structures may be equipped with sensors to passively or actively monitor the surrounding environment (e.g., street cameras, traffic cameras, and other sensors).

In example embodiments, the attribute data may include data associated with the third party sources 1460. The third party sources 1460 may also provide an abundance of data associated with the user. For instance, the attribute data may include data accessed from government websites or other public records that may provide criminal histories, civil citation histories, credit histories, or other publicly available information.

In various embodiments, a smart home is a house, office, or other environment of the user with one or more smart devices integrated throughout. Nearly every facet of the smart home may provide data associated with the user (e.g., via the smart device acting as sensors to provide various data). In some implementations, the attribute data includes data corresponding to the home sources 1470. For instance, the home sources 1470 may include smart appliances, consumables, utilities, and many other smart devices. In a few specific instances, the attribute data may include consumable inventories and consumption rates of various consumable goods (e.g., perishables such as milk or bread) tracked, monitored, or otherwise observed by smart refrigerators. In another instance, the attribute data may include utility usage data (e.g., electricity, water). Analysis of the utility usage data may indicate patterns or a status of the user, such as the user being on vacation, the user being ill (e.g., increasing house thermostat set temperature to cope with a cold), the user being an energy conscious consumer, and so on.

Figure 15:
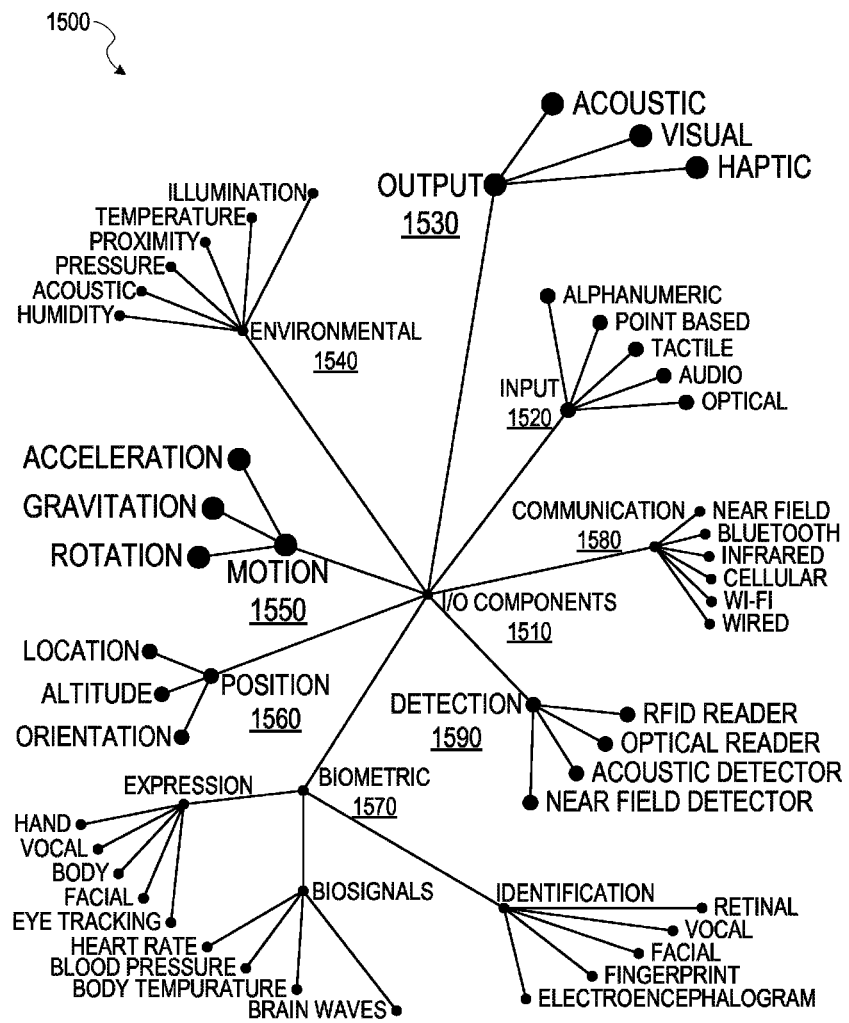
FIG. 15 depicts various components that provide attribute data, according to some example embodiments.

Referring now to FIG. 15, example diagram 1500 depicts non-limiting example I/O components 1510 that may provide attribute data, according to some example embodiments. In example embodiments, the I/O components 1510 include input components 1520, output components 1530, environmental components 1540, motion components 1550, position components 1560, biometric components 1570, communication components 1580, detection components 1590, and a wide gamut of other sensors, gauges, and measurement components not shown in FIG. 15. The I/O components 1510 or a suitable combination of the I/O components 1510 may be included in any suitable device or machine such as those included in the attribute sources 1410 depicted in FIG. 14 to facilitate the functionality described herein.

The I/O components 1510 may receive, detect, measure, capture, or otherwise obtain sensor data associated with physical properties, attributes, or characteristics. The I/O components 1510 may provide, produce, transmit, or otherwise communicate the sensor data or other indications associated with the physical properties, attributes, or characteristics (e.g., a sensor included in a device operable to communicate the sensor data to the networked system 102). In some implementations, a combination of devices may be employed to provide the sensor data (e.g., a first device that includes a sensor and is communicatively coupled to a second device that communicates sensor data received from the first device to the networked system 102). As a result, the sensor data provided by the I/O components 1510 may be accessible to all, or some, of the modules described above on a real-time or near real-time basis. The I/O components 1510 are grouped according to functionality merely for simplifying the following discussion and the grouping is in no way limiting.

The input components 1520 include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and force of touches or touch gestures, or other tactile input components), audio input components e.g., a microphone), and the like. In some implementations, the input components 1520 receive input from the user to facilitate the functionalities described herein. For instance, the user may interact with a user interface using the input components 1520.

The output components 1530 include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor), other signal generators, and so forth. The output components 1530 may present information to the user. For example, the output components 1530 may present a user interface to the user or present media files to the user.

The environmental components 1540 include illumination sensors (e.g., photometer), temperature sensors (e.g., one or more thermometers that detect ambient temperature), humidity sensors, pressure sensors (e.g., barometer), acoustic sensors (e.g., one or more microphones that detect background noise), proximity sensors (e.g., an infrared sensor that detects nearby objects), gas sensors (e.g., machine olfaction detection sensors, gas detection sensors to detect concentrations of hazardous gases for safety or to measure pollutants in the atmosphere), and so on. The environmental components 1540 may measure various physical parameters to provide an indication or signal corresponding to the physical environment surrounding the environmental components 1540.

The motion components 1550 include acceleration sensors (e.g., accelerometer), gravitation sensors, rotation sensors (e.g., gyroscope), and so forth. The motion components 1550 may provide motion data such as velocity, acceleration, or other force measurements along an x, y, and z axes. In some implementations, the motion data is provided at a regular update rate or sampling rate (e.g., 10 updates per second) that may be configurable.

The position components 1560 include location sensors (e.g., a Global Position System (GPS) receiver component), altitude sensors (e.g., altimeters or barometers that detect air pressure from which altitude may be derived), orientation sensors (e.g., magnetometers that provide magnetic field strength along the x, y, and z axes), and the like. In an example embodiment, the position components 1560 may provide position data such as latitude, longitude, altitude, and a time stamp. Similar to the motion components 1550, the position components 1560 may provide the motion data at a regular update rate that may be configurable.

The biometric components 1570 include components to detect expressions, measure biosignals, or identify people, among other functions. For example, the biometric components 1570 include expression components to detect expressions (also referred to as "kinesics") such as hand gestures (e.g., an optical component to detect a hand gesture or a Doppler component to detect hand motions), vocal expressions (e.g., a microphone to detect changes in voice pitch that may indicate tension), facial expressions (e.g., a camera to detect expressions or micro-expressions of a person such as a smile), body gestures, and eye tracking (e.g., detecting the focal point of a person's eyes or patterns in eye movement). The biometric components 1570 may also include, for example, biosignal components to measure biosignals such as blood pressure, heart rate, body temperature, perspiration, and brain waves (e.g., as determined by a electroencephalogram). In further examples, the biometric components 1570 include identification components to identify people such as retinal scanners (e.g., a camera component), vocal detectors (e.g., a microphone to receive audio data for voice identification), facial detectors, fingerprint detectors, and electroencephalogram sensors (e.g., to identify a person via unique brain wave patterns).

Communication may be implemented using a wide variety of technologies. The I/O components 1510 may include communication components 1580 operable to communicatively couple machines or devices. For example, the communication components 1580 may include a network interface component or other suitable device to interface with a network (e.g., the network 104). In further examples, the communication components 1580 may include wired communication components, wireless communication components, cellular communication components, Near Field Communication (NFC) components, Bluetooth® components (e.g., Bluetooth® Low Energy), Wi-Fi® components, and other communication components to provide communication via other modalities. In addition, a variety of information may be derived using the communication components 1580 such as location via Internet Protocol (IP) geo-location, location via Wi-Fi® signal triangulation, location via detecting a NFC beacon signal that may indicate a particular location, and on forth.

The detection components 1590 provide functionality to detect a variety of identifiers. For example, the detection components 1590 include Radio Frequency Identification (RFID) tag reader components, Near Field Communication (NFC) smart tag detection components, optical reader components (e.g., an optical sensor to detect one-dimensional bar codes such as Universal Product Code (UPC) bar codes, multi-dimensional bar codes such as a Quick Response (QR) code, Aztec code, Data Matrix, Dataglyph, MaxiCode, PDF417, Ultra Code, Uniform Commercial Code Reduced Space Symbology (UCC RSS)-2D bar code, and other optical codes), or acoustic detection components (e.g., microphones to identify tagged audio signals). In addition, a variety of information may be derived via various communication components such as location via Internet Protocol (IP) geo-location, location via Wi-Fi® signal triangulation, location via detecting a NFC beacon signal that may indicate a particular location, and so forth.

Figure 16:
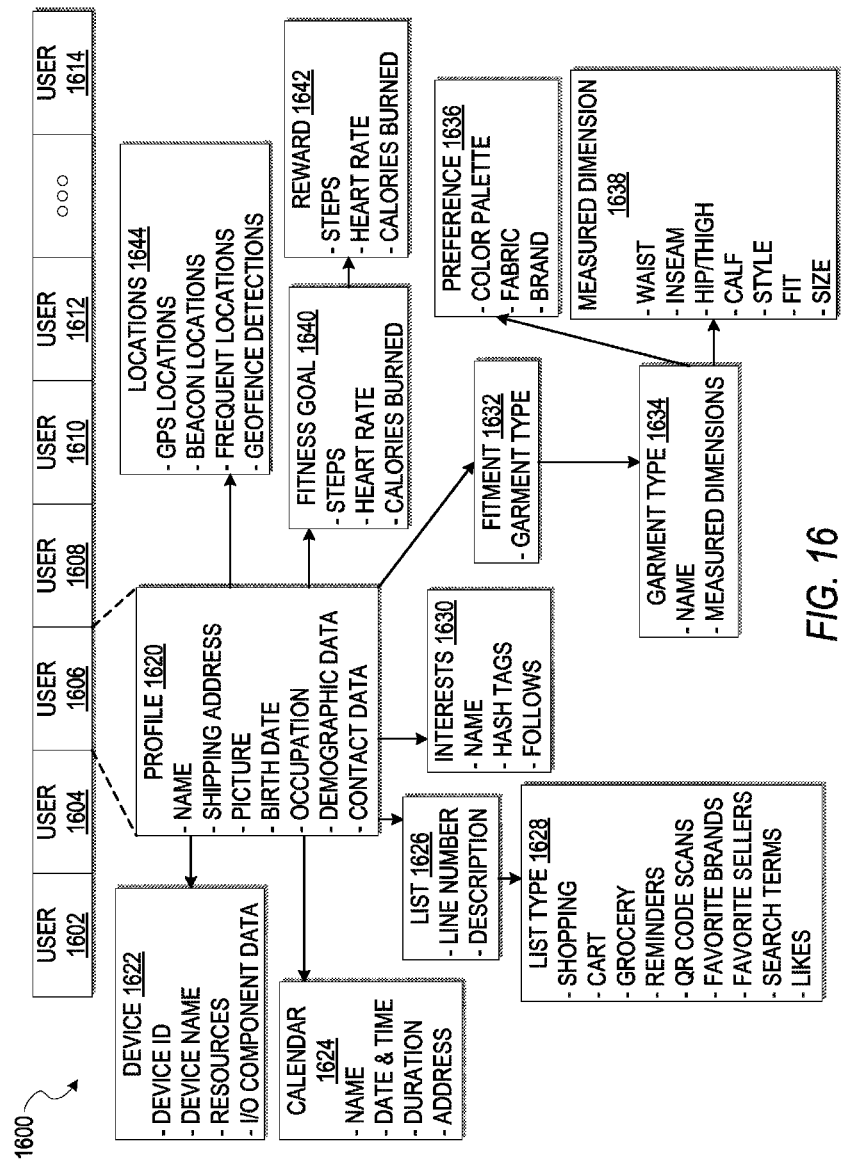
FIG. 16 is a block diagram of an example data structure for example attribute data associated with a user, according to some example embodiments.

FIG. 16 is a block diagram 1600 of an example data structure for the attribute data associated with a particular user according to example embodiments. In embodiments, the attribute data is associated with a plurality of users such as user 1602, 1604, 1606, 1608, 1610, 1612, and 1614. In an embodiment, the attribute data is accessed for a particular user via a lookup using a user identifier. The attribute data includes, for example, profile data 1620, device data 1622, calendar data 1624, list data 1626, list type data 1628, interest data 1630, fitment data 1632, garment type data 1634, preference data 1636, measured dimension data 1638, fitness goal data 1640, reward data 1642, location data 1644, and other data not shown in FIG. 16. In some embodiments, the attribute data may be structured such that various portions of the attribute data are associated with other portions of the attribute data via relationships. For instance, the calendar data 1624 may include a calendar event associated with an event name, an event data, and an event location for the calendar event.

Figure 17:
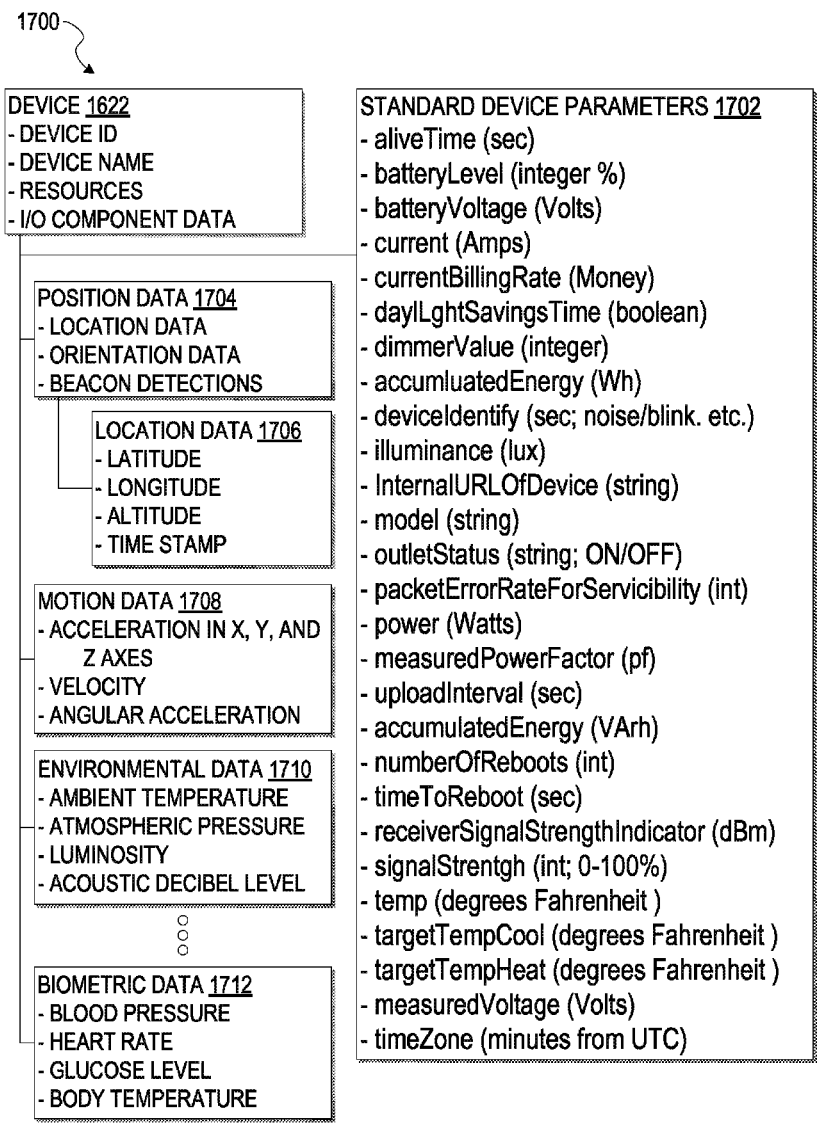
FIG. 17 is a block diagram of an example data structure for example attribute data associated with a device, according to some example embodiments.

FIG. 17 is a block diagram 1700 of an example data structure for data associated with a device according to some example embodiments. In an example embodiment, the device data 1622 of FIG. 16 may include a device identifier, a device name, device resources data (e.g., files stores on the devices such as browser cookies, media files), I/O component data, and so forth. In example embodiments, the device identifier comprises, for example, an Internet Protocol (IP) address, a Media Access Control (MAC) address, other unique identifiers, an International Mobile Station Equipment identity (IMEI), or a Mobile Equipment Identifier (MEID). In an embodiment, the I/O component data includes standard device parameters 1702, position data 1704, location data 1706, motion data 1708, environmental data 1710, biometric data 1712, among other data. FIG. 17 merely depicts example attribute data that may correspond to a particular device, and a variety of other data not shown in FIG. 17 may be included in the device data. In various embodiments, the standard device parameters 1702 include parameters that are standard across multiple devices included in the IoT. In some embodiments, standardized parameters and protocols facilitate access and utilization of the attribute data corresponding to such devices. For example, the attribute data available on an unknown device may be accessed and utilized without the need to discover or otherwise determine which parameters are available and which units of measure are associated with the parameters.

Many other schemes may be employed to discover or otherwise determine available parameters accessible on a particular device.

MODULES, COMPONENTS, AND LOGIC

Certain embodiments are described herein as including logic or a number of components, modules, or mechanisms. Modules may constitute either software modules (e.g., code embodied on a machine-readable medium or in a transmission signal) or hardware modules. A "hardware module" is a tangible unit capable of performing certain operations and may be configured or arranged in a certain physical manner. In various example embodiments, one or more computer systems (e.g., a standalone computer system, a client computer system, or a server computer system) or one or more hardware modules of a computer system (e.g., a processor or a group of processors) may be configured by software (e.g., an application or application portion) as a hardware module that operates to perform certain operations as described herein.

In some embodiments, a hardware module may be implemented mechanically, electronically, or any suitable combination thereof. For example, a hardware module may include dedicated circuitry or logic that is permanently configured to perform certain operations. For example, a hardware module may be a special-purpose processor, such as a Field-Programmable Gate Array (FPGA) or an Application Specific Integrated Circuit (AMC). A hardware module may also include programmable logic or circuitry that is temporarily configured by software to perform certain operations. For example, a hardware module may include software encompassed within a general-purpose processor or other programmable processor. It will be appreciated that the decision to implement a hardware module mechanically, in dedicated and permanently configured circuitry, or in temporarily configured circuitry (e.g., configured by software) may be driven by cost and time considerations.

Accordingly, the phrase "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where a hardware module comprises a general-purpose processor configured by software to become a special-purpose processor, the general-purpose processor may be configured as respectively different special-purpose processors (e.g., comprising different hardware modules) at different times, Software may accordingly configure a particular processor or processors, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple hardware modules exist contemporaneously, communications may be achieved through signal transmission (e.g., over appropriate circuits and buses) between or among two or more of the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions described herein. As used herein, "processor-implemented module" refers to a hardware module implemented using one or more processors.

Similarly, the methods described herein may be at least partially processor-implemented, with a particular processor or processors being an example of hardware. For example, at least some of the operations of a method may be performed by one or more processors or processor-implemented modules. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented modules may be located in a single geographic location (e.g., within a home environment, an office environment, or a server farm). In other example embodiments, the processors or processor-implemented modules may be distributed across a number of geographic locations.

SOFTWARE ARCHITECTURE

Figure 18:
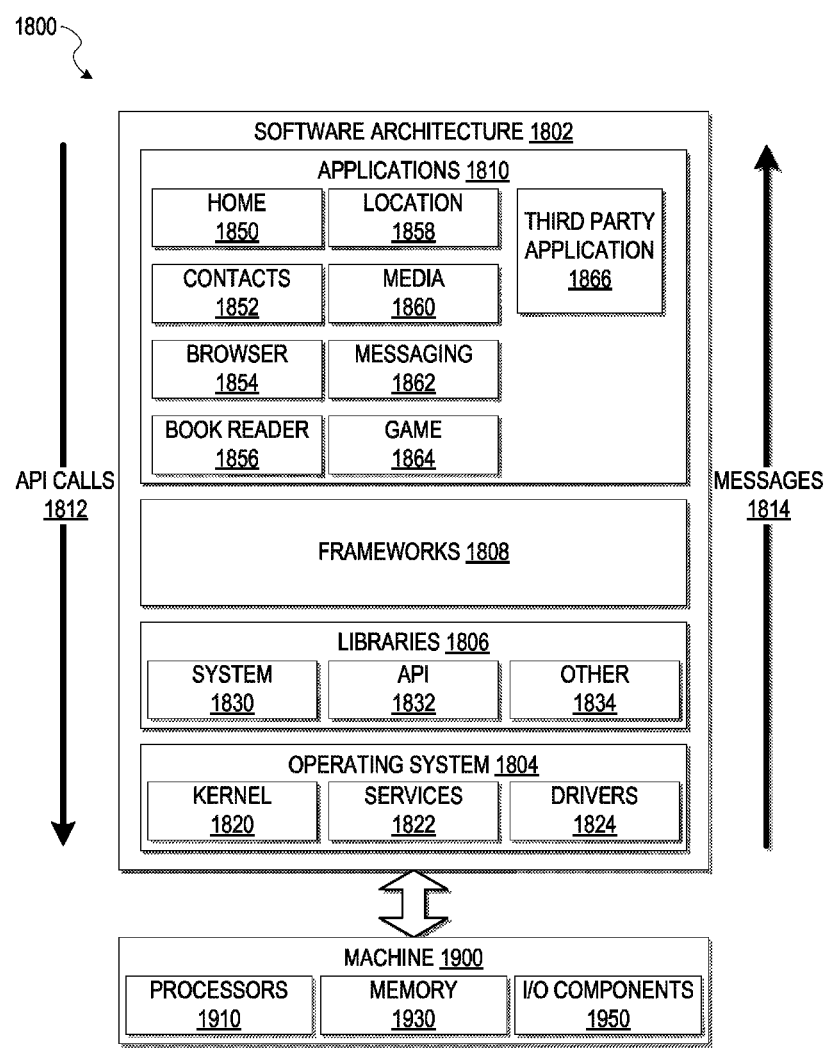
FIG. 18 is a block diagram illustrating an example of a software architecture that may be installed on a machine, according to some example embodiments.

FIG. 18 is a block diagram 1800 illustrating an architecture of software 1802, which may be installed on any one or more of the devices described above. FIG. 18 is merely a non-limiting example of a software architecture, and it will be appreciated that many other architectures may be implemented to facilitate the functionality described herein. The software 1802 may be implemented by hardware such as machine 1900 of FIG. 19 that includes processors 1910, memory 1930, and I/O components 1950. In this example architecture, the software 1802 may be conceptualized as a stack of layers where each layer may provide a particular functionality. For example, the software 1802 includes layers such as an operating system 1804, libraries 1806, frameworks 1808, and applications 1810. Operationally, the applications 1810 invoke application programming interface (API) calls 1812 through the software stack and receive messages 1814 in response to the API calls 1812, according to some implementations.

In various implementations, the operating system 1804 manages hardware resources and provides common services. The operating system 1804 includes, for example, a kernel 1820, services 1822, and drivers 1824. The kernel 1820 acts as an abstraction layer between the hardware and the other software layers in some implementations. For example, the kernel 1820 provides memory management, processor management (e.g., scheduling), component management, networking, security settings, among other functionality. The services 1822 may provide other common services for the other software layers. The drivers 1824 may be responsible for controlling or interfacing with the underlying hardware. For instance, the drivers 1824 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth.

In some implementations, the libraries 1806 provide a low-level common infrastructure that may be utilized by the applications 1810. The libraries 1806 may include system 1830 libraries (e.g., C standard library) that may provide functions such as memory allocation functions, string manipulation functions, mathematic functions, and the like. In addition, the libraries 1806 may include API libraries 1832 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 1806 may also include a wide variety of other libraries 1834 to provide many other APIs to the applications 1810.

The frameworks 1808 provide a high-level common infrastructure that may be utilized by the applications 1810, according to some implementations. For example, the frameworks 1808 provide various graphic user interface (GUI) functions, high-level resource management, high-level location services, and so forth. The frameworks 1808 may provide a broad spectrum of other APIs that may be utilized by the applications 1810, some of which may be specific to a particular operating system or platform.

In an example embodiment, the applications 1810 include a home application 1850, a contacts application 1852, a browser application 1854, a book reader application 1856, a location application 1858, a media application 1860, a messaging application 1862, a game application 1864, and a broad assortment of other applications such as third party application 1866. According to some embodiments, the applications 1810 are programs that execute functions defined in the programs. Various programming languages may be employed to create one or more of the applications 1810, structured in a variety of manners, such as object-orientated programming languages (e.g., Objective-C, Java, or C++) or procedural programming languages (e.g., C or assembly language). In a specific example, the third party application 1866 (e.g., an application developed using the Android™ or iOS™ software development kit (SDK) by an entity other than the vendor of the particular platform) may be mobile software running on a mobile operating system such as iOS™, Android™, Windows® Phone, or other mobile operating systems. In this example, the third party application 1866 may invoke the API calls 1812 provided by the mobile operating system 1804 to facilitate functionality described herein.

EXAMPLE MACHINE ARCHITECTURE AND MACHINE-READABLE MEDIUM

Figure 19:
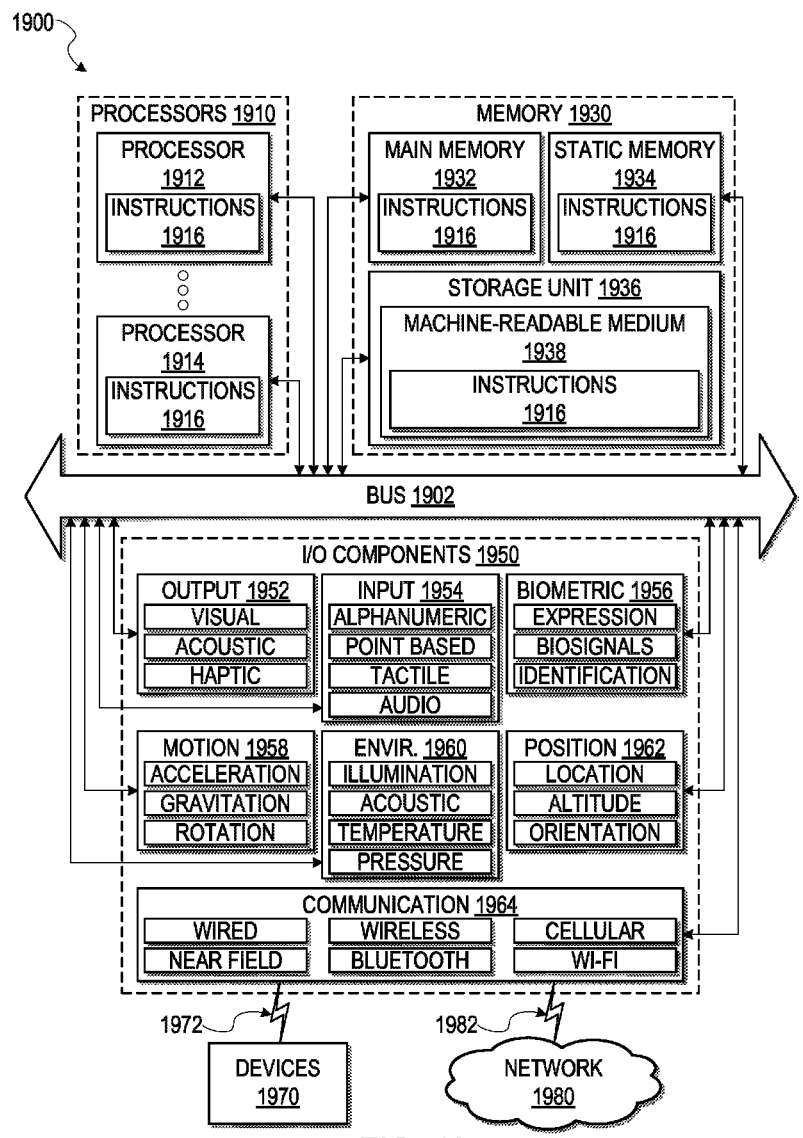
FIG. 19 illustrates a diagrammatic representation of a machine in the form of a computer system within which a set of instructions may be executed for causing the machine to perform any one or more of the methodologies discussed herein, according to an example embodiment.

FIG. 19 is a block diagram illustrating components of a machine 1900, according to some example embodiments, able to read instructions from a machine-readable medium (e.g., a machine-readable storage medium) and perform any one or more of the methodologies discussed herein. Specifically, FIG. 19 shows a diagrammatic representation of the machine 1900 in the example form of a computer system, within which instructions 1916 (e.g., software, a program, an application, an applet, an app, or other executable code) for causing the machine 1900 to perform any one or more of the methodologies discussed herein may be executed. In alternative embodiments, the machine 1900 operates as a standalone device or may be coupled (e.g., networked) to other machines. In a networked deployment, the machine 1900 may operate in the capacity of a server machine or a client machine in a server-client network environment, or as a peer machine in a peer-to-peer (or distributed) network environment. The machine 1900 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1916, sequentially or otherwise, that specify actions to be taken by machine 1900. Further, while only a single machine 1900 is illustrated, the term "machine" shall also be taken to include a collection of machines 1900 that individually or jointly execute the instructions 1916 to perform any one or more of the methodologies discussed herein.

The machine 1900 may include processors 1910, memory 1930, and I/O components 1950, which may be configured to communicate with each other via a bus 1902. In an example embodiment, the processors 1910 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, processor 1912 and processor 1914 that may execute instructions 1916. The term "processor" is intended to include multi-core processors that may comprise two or more independent processors (also referred to as "cores") that may execute instructions contemporaneously. Although FIG. 19 shows multiple processors, the machine 1900 may include a single processor with a single core, a single processor with multiple cores (e.g., a multi-core process), multiple processors with a single core, multiple processors with multiples cores, or any combination thereof.

The memory 1930 may include a main memory 1932, a static memory 1934, and a storage unit 1936 accessible to the processors 1910 via the bus 1902. The storage unit 1936 may include a machine-readable medium 1938 on which is stored the instructions 1916 embodying any one or more of the methodologies or functions described herein. The instructions 1916 may also reside, completely or at least partially, within the main memory 1932, within the static memory 1934, within at least one of the processors 1910 (e.g., within the processor's cache memory), or any suitable combination thereof, during execution thereof by the machine 1900. Accordingly, in various implementations, the main memory 1932, static memory 1934, and the processors 1910 are considered as machine-readable media 1938.

As used herein, the term "memory" refers to a machine-readable medium 1938 able to store data temporarily or permanently and may be taken to include, but not be limited to, random-access memory (RAM), read-only memory (ROM), buffer memory, flash memory, and cache memory. While the machine-readable medium 1938 is shown in an example embodiment to be a single medium, the term "machine-readable medium" should be taken to include a single medium or multiple media (e.g., a centralized or distributed database, or associated caches and servers) able to store instructions 1916. The term "machine-readable medium" shall also be taken to include any medium, or combination of multiple media, that is capable of storing instructions (e.g., instructions 1916) for execution by a machine (e.g., machine 1900), such that the instructions, when executed by one or more processors of the machine 1900 (e.g., processors 1910), cause the machine 1900 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" shall accordingly be taken to include, but not be limited to, one or more data repositories in the form of a solid-state memory (e.g., flash memory), an optical medium, a magnetic medium, other non-volatile memory e.g., Erasable Programmable Read-Only Memory (EPROM)), or any suitable combination thereof. The term "machine-readable medium" specifically excludes non-statutory signals per se.

The I/O components 1950 include a wide variety of components to receive input, provide output, produce output, transmit information, exchange information, capture measurements, and so on. In general, it will be appreciated that the I/O components 1950 may include many other components that are not shown in FIG. 19. The I/O components 1950 are grouped according to functionality merely for simplifying the following discussion and the grouping is in no way limiting. In various example embodiments, the I/O components 1950 include output components 1952 and input components 1954, The output components 1952 include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor), other signal generators, and so forth. The input components 1954 include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and force of touches or touch gestures, or other tactile input components), audio input components (e.g., a microphone), and the like.

In some further example embodiments, the I/O components 1950 include biometric components 1956, motion components 1958, environmental components 1960, or position components 1962 among a wide array of other components. For example, the biometric components 1956 include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1958 include acceleration sensor components (e.g., accelerometer), gravitation sensor components, rotation sensor components (e.g., gyroscope), and so forth. The environmental components 1960 include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., machine olfaction detection sensors, gas detection sensors to detection concentrations of hazardous gases for safety or to measure pollutants in the atmosphere), or other components that may provide indications, measurements, or signals corresponding to a surrounding physical environment. The position components 1962 include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1950 may include communication components 1964 operable to couple the machine 1900 to a network 1980 or devices 1970 via coupling 1982 and coupling 1972, respectively. For example, the communication components 1964 include a network interface component or another suitable device to interface with the network 1980. In further examples, communication components 1964 include wired communication components, wireless communication components, cellular communication components, Near Field Communication (NEC) components, Bluetooth® components (e.g., Bluetooth® Low Energy), Wi-Fi® components, and other communication components to provide communication via other modalities. The devices 1970 may be another machine or any of a wide variety of peripheral devices (e.g., a peripheral device coupled via a Universal Serial Bus (USB)).

Moreover, in some implementations, the communication components 1964 detect identifiers or include components operable to detect identifiers. For example, the communication components 1964 include Radio Frequency Identification (MD) tag reader components, NEC smart tag detection components, optical reader components (e.g., an optical sensor to detect a one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, Uniform Commercial Code Reduced Space Symbology (UCC RSS)-2D bar code, and other optical codes), acoustic detection components (e.g., microphones to identify tagged audio signals), or any suitable combination thereof. In addition, a variety of information can be derived via the communication components 1964, such as, location via Internet Protocol (IP) geo-location, location via Wi-Fi® signal triangulation, location via detecting a NFC beacon signal that may indicate a particular location, and so forth.

TRANSMISSION MEDIUM

In various example embodiments, one or more portions of the network 1980 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 1980 or a portion of the network 1980 may include a wireless or cellular network and the coupling 1982 may be a Code Division Multiple Access (CDMA) connection, a Global System for Mobile communications (GSM) connection, or other type of cellular or wireless coupling. In this example, the coupling 1982 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

In example embodiments, the instructions 1916 are transmitted or received over the network 1980 using a transmission medium via a network interface device (e.g., a network interface component included in the communication components 1964) and utilizing any one of a number of well-known transfer protocols (e.g., Hypertext Transfer Protocol (HTTP)). Similarly, in other example embodiments, the instructions 1916 are transmitted or received using a transmission medium via the coupling 1972 (e.g., a peer-to-peer coupling) to devices 1970. The term "transmission medium" shall be taken to include any intangible medium that is capable of storing, encoding, or carrying instructions 1916 for execution by the machine 1900, and includes digital or analog communications signals or other intangible medium to facilitate communication of such software.

Furthermore, the machine-readable medium 1938 is non-transitory (in other words, not having any transitory signals) in that it does not embody a propagating signal. However, labeling the machine-readable medium 1938 as "non-transitory" should not be construed to mean that the medium is incapable of movement; the medium should be considered as being transportable from one physical location to another. Additionally, since the machine-readable medium 1938 is tangible, the medium may be considered to be a machine-readable device.

LANGUAGE

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is claimed is:

1. An electronic device comprising:
one or more hardware processors, and
a memory having stored therein instructions that, when executed by the one or more hardware processors, cause the electronic device to perform operations comprising:
detecting a device activity being performed in real-time by a primary user device of a user;
accessing attribute data associated with the user from a plurality of attribute sources;
inferring a user preference, from the attribute data, indicating a preference of the user for performing on a secondary user device an ancillary activity corresponding to the device activity;
based on the inferred user preference, identifying, using the one or more hardware processors, the secondary user device according to a device status of the secondary user device that indicates a device capability to perform the ancillary activity in real-time;

based on a comparison between an inferred current location of the user and location data received from the secondary user device, determining whether the secondary user device is within an operable distance of the user for the ancillary activity, the inferred current location of the user based on location data received from the primary user device;

generating the ancillary activity, to be performed in real-time on the secondary user device, by analysis of the device activity, a device functionality of the secondary user device, a determination that the secondary user device is within the operable distance of the user for the ancillary activity, and the user preference, the generating of the complementary activity comprising comparing the device functionality of the secondary user device with a device functionality of the primary user device to identify non-mutual functionality of the secondary user device that is not available on the primary user device, the non-mutual functionality of the secondary user device including functionality to capture data from a sensor not available on the primary user device, the complementary activity to include an activity component that utilizes the non-mutual functionality of the secondary user device; and causing performance of the ancillary activity on the secondary user device in real-time.

2. The system of claim 1, wherein the operations further comprise receiving, from the secondary user device, sensor data that represents a real-time physical environment of the secondary user device and determining the device status of the secondary user device by analysis of the sensor data.

3. A method comprising:
detecting a device activity being performed in real-time by a primary user device of a user;
accessing attribute data associated with the user from a plurality of attribute sources;
inferring a user preference, from the attribute data, indicating a preference of the user for performing on a secondary user device a complementary activity corresponding to the device activity;
based on the inferred user preference, identifying, using a hardware processor of a machine, the secondary user device according to a device status of the secondary user device indicating a device capability to perform the complementary activity in real-time;
based on a comparison between an inferred current location of the user and location data received from the secondary user device, determining whether the secondary user device is within an operable distance of the user for the complementary activity, the inferred current location of the user based on location data received from the primary user device;
generating the complementary activity, to be performed in real-time on the secondary user device, by analyzing the device activity, a device functionality of the secondary user device, a determination that the secondary user device is within the operable distance of the user for the complementary activity, and the user preference, the generating of the complementary activity comprising comparing the device functionality of the secondary user device with a device functionality of the primary user device to identify non-mutual functionality of the secondary user device that is not available on the primary user device, the non-mutual functionality of the secondary user device including functionality to capture data from a sensor not available on the primary user device, the complementary activity to include an activity component that utilizes the non-mutual functionality of the secondary user device; and transmitting, to the secondary user device, instructions to perform in real-time the complementary activity.

4. The method of claim 3, further comprising:
receiving, from the secondary user device, sensor data representing a real-time physical environment of the secondary user device; and
determining the device status of the secondary user device by analyzing the sensor data.

5. The method of claim 3, further comprising:
augmenting the device activity being performed in real-time by the primary user device based on the generated complementary activity.

6. The method of claim 3, wherein the secondary device comprises a wearable computing device.

7. The method of claim 3, wherein the complementary activity comprises a portion of the device activity.

8. The method of claim 3, wherein the complementary activity comprises a notification including notification content that corresponds to the device activity.

9. The method of claim 3, further comprising:
wherein the device functionality includes a display size corresponding to the secondary user device;
determining the display size corresponding to the secondary user device is below a threshold size; and
generating the complementary activity to include abridged activity content according to the display size corresponding to the secondary user device.

10. The method of claim 3, further comprising:
identifying a plurality of user devices based on respective device statuses of the plurality of user devices, each device status of the device statuses indicating capability to perform a particular complementary activity in real-time; and
determining a suitable user device from among the plurality of user devices based on the user preference and a determination that the suitable user device is within an operable distance of the user for the complementary activity based on the inferred current location of the user, the suitable user device being capable of performing the complementary activity in real-time.

11. The method of claim 3, further comprising:
inferring user characteristics pertaining to the user from the attribute data;
identifying similar users, from among a plurality of other users, that are similar to the user based on the inferred user characteristics and respective user characteristics of the plurality of other users; and
inferring the user preference based on the user characteristics of the identified similar users and the inferred user characteristics.

12. A machine-readable medium having no transitory signals and storing instructions that, when executed by at least one processor of a machine, cause the machine to perform operations comprising:
detecting a device activity being performed in real-time by a primary user device of a user;
accessing attribute data associated with the user from a plurality of attribute sources;

inferring a user setting, from the attribute data, indicating a preference of the user for performing on a secondary user device a companion activity corresponding to the device activity;

based on the inferred user setting, identifying, using a hardware processor of a machine, the secondary user device according to a device status of the secondary user device indicating a device capability to perform the companion activity in real-time;

based on a comparison between an inferred current location of the user and location data received from the secondary user device, determining whether the secondary user device is within an operable distance of the user for the companion activity, the inferred current location of the user based on location data received from the primary user device;

generating the companion activity, to be performed in real-time on the secondary user device, by analyzing the device activity, a device functionality of the secondary user device, a determination that the secondary user device is within the operable distance of the user for the companion activity, and the user setting, the generating of the companion activity comprising comparing the device functionality of the secondary user device with a device functionality of the primary user device to identify non-mutual functionality of the secondary user device that is not available on the primary user device, the non-mutual functionality of the secondary user device including functionality to capture data from a sensor not available on the primary user device, the companion activity to include an activity component that utilizes the non-mutual functionality of the secondary user device; and causing performance of the companion activity on the secondary user device in real-time.

13. The machine-readable medium of claim 12, further comprising:

receiving, from the secondary user device, sensor data representing a real-time physical environment of the secondary user device; and determining the device status of the secondary user device by analyzing the sensor data.

14. The machine-readable medium of claim 12, further comprising:

augmenting the device activity being performed in real-time by the primary user device based on the generated companion activity.

* * * * *